(12) United States Patent
Seitz et al.

(10) Patent No.: US 6,548,549 B1
(45) Date of Patent: *Apr. 15, 2003

(54) ACYLAMINOSALICYLIC ACID AMIDES AND THEIR USES AS PESTICIDES

(75) Inventors: Thomas Seitz, Langenfeld (DE); Klaus Naumann, Leverkusen (DE); Ralf Tiemann, Leverkusen (DE); Klaus Stenzel, Düsseldorf (DE); Gerd Hänssler, Leverkusen (DE); Stefan Dutzmann, Langenfeld (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/400,655

(22) Filed: Sep. 21, 1999

Related U.S. Application Data

(62) Division of application No. 09/029,110, filed as application No. PCT/EP96/03637 on Aug. 19, 1996, now Pat. No. 6,001,879.

(30) Foreign Application Priority Data

Aug. 30, 1995 (DE) .......................................... 195 31 891
Apr. 19, 1996 (DE) .......................................... 196 15 453
Jul. 1, 1996 (DE) .......................................... 196 26 311

(51) Int. Cl.$^7$ ...................... C07D 237/14; A01N 37/18
(52) U.S. Cl. ........................ 514/619; 564/166; 564/167
(58) Field of Search ............................... 564/166, 167; 514/619

(56) References Cited

U.S. PATENT DOCUMENTS

| | | | | |
|---|---|---|---|---|
| 3,309,267 A | * | 3/1967 | Starkey | 167/30 |
| 3,577,550 A | * | 5/1971 | Moyle | 424/324 |
| 4,146,631 A | * | 3/1979 | Ford | 424/269 |

OTHER PUBLICATIONS van Tamelen, JACS 83 1639, Apr. 1961.*

* cited by examiner

*Primary Examiner*—Robert Gerstl
(74) *Attorney, Agent, or Firm*—Norris, McLaughlin & Marcus

(57) ABSTRACT

The invention relates to known and to new acylaminosalicylamides, to a plurality of processes for their preparation and to their use as pesticides. The present application furthermore relates to new intermediates, to a plurality of processes for their preparation and to their use as pesticides.

9 Claims, No Drawings

ACYLAMINOSALICYLIC ACID AMIDES AND THEIR USES AS PESTICIDES

This is a divisional application of U.S. Ser. No. 09/029,110, filed on Feb. 18, 1998, now U.S. Pat. No. 6,001,879, which is a 371 of PCT/EP96/03637 filed Aug. 19, 1996.

The invention relates to known and to new acylaminosalicylamides, to a plurality of processes for their preparation and to their use as pesticides. The present application furthermore relates to novel intermediates, to a plurality of processes for their preparation and to their use as pesticides.

Certain acylaminosalicylamides, such as, for example, the compounds 3-formamido-salicylanilide and 3-(formylamino)-2-hydroxy-N-(phenylmethyl)-benzamide, have already been disclosed (compare, for example, B. Biochim. Biophys. Acta (1993), 1143(3), 262–8, J. Med. Chem. (1990), 33(1), 136–42 or J. Biol. Chem. (1971), 246(23), 7125–30).

However, an activity against pests has not been described to date of these prior-art compounds.

It has now been found that the acylaminosalicylamides of the general formula (I)

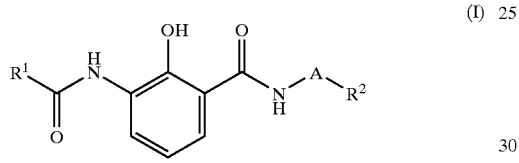

in which
A represents a single linkage or an alkylene chain,
$R^1$ represents hydrogen, alkyl or alkoxy,
$R^2$ represents in each case optionally substituted cyloalkyl, cycloalkenyl, aryl or heterocyclyl
are suitable for controlling pests, preferably fungi, insects and bacteria, in plants and industrial materials.

In the definitions, the hydrocarbon chains such as alkyl, alkene, alkenyl or alkinyl, also in conjunction with hetero atoms such as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

Aryl represents aromatic, mono- or polycyclic hydrocarbon rings such as, for example, phenyl, naphthyl, anthranyl, phenanthryl, preferably phenyl or naphthyl, in particular phenyl.

Heterocyclyl represents saturated or unsaturated and also aromatic, cyclic compounds having up to eight ring members in which at least one ring member is a hetero atom, that is to say an atom other than carbon. If the ring contains more than one hetero atom, they can be identical or different. Hetero atoms are preferably oxygen, nitrogen or sulphur. If appropriate, the cyclic compounds together with other carbocyclic or heterocyclic, fused or bridged rings form a polycyclic ring system. Mono- or bicyclic ring systems are preferred, in particular mono- or bicyclic aromatic ring systems.

Cycloalkyl represents saturated carbocyclic cyclic compounds which, if appropriate, together with other carbocyclic, fused or bridged rings form a polycyclic ring system.

Cycloalkenyl represents carboxycyclic cyclic compounds which contain at least one double bond and, if appropriate, together With other carbocyclic, fused or bridged rings form a polycyclic ring system The present application also relates to new acylaminosalicylamides of the general formula (I)

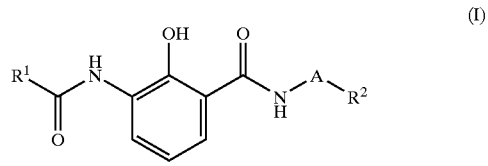

in which
A represents a single linkage or optionally substituted alkylene,
$R^1$ represents hydrogen, alkyl or alkoxy,
$R^2$ represents in each case optionally substituted cyloalkyl, cycloalkenyl, aryl or heterocyclyl, with the exception of the nitro group as substituent,
and the compounds 3-(formylamino)-2-hydroxy-N-{4-[2,4,6-tris(1-methylpropyl)-phenoxylphenyl}-benzamide, N-{4-[3,5-bis-(1,1-dimethylethyl)-phenoxy]-phenyl}-3-(formylamino)-2-hydroxy-benzamide, N-{4-[2,4-bis-(1,1-dimethylethyl)-phenoxy]-phenyl}-3-(formylamino)-2-hydroxy-benzamide, N-{4-[2,6-bis-(1-methylpropyl)-phenoxy]-phenyl}-3-(formylamino)-2-hydroxy-benzamide, 3-(formylamino)-2-hydroxy-N-{4-[3-(trifluoromethyl)-phenoxy]-phenyl}-benzamide, N-{4-[4-(1,1-dimethylethyl)-phenoxy]-phenyl}-3-(formylamino)-2-hydroxy-benzamide, 3-(formylamino)-2-hydroxy-N-(4-phenoxyphenyl)-benzamide, N-(4-butylphenyl)-3-(formylamino)-2-hydroxy-benzamide and N-{3-chloro-4-(4-chlorophenoxy)phenyl}-3-(formylamino)-2-hydroxy-benzamide, 3-(formylamino)-2-hydroxy-N-(phenylmethyl)-benzamide, 3-formamidosalicylanilide and 3-(formylamino)-2-hydroxy-N-(2-phenylethyl)-benzamide are excepted.

Furthermore, it has been found that the new acylaminosalicylamides of the general formula (I) are obtained when a) aminosalicylamides of the general formula (II)

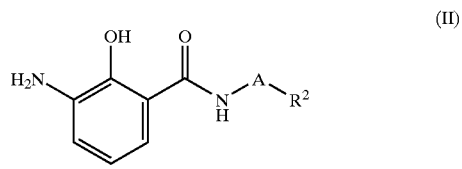

in which
A and $R^2$ have the abovementioned meanings
are reacted with acylating agents of the general formula (III)

in which
$R^1$ has the abovementioned meaning and
$X^1$ represents halogen, hydroxyl, alkoxy or alkylcarbonyloxy,
if appropriate in the presence of a diluent, if appropriate in the presence of an acid acceptor and if appropriate in the presence of a further reaction auxiliary, or when b) nitrosalicylamides of the general formula (IV)

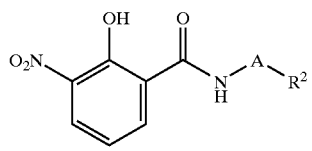

(IV)

in which

A and R² have the abovementioned meanings
are reacted with formic acid, if appropriate in the presence of a catalyst and if appropriate in the presence of further reaction auxiliary, or when c) O-benzyl-nitrosalicylamides of the general formula (V)

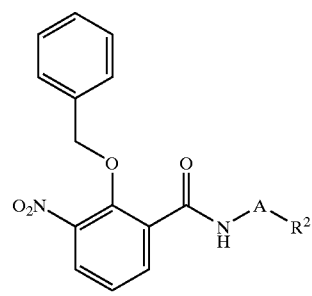

(V)

in which

A and R² have the abovementioned meanings
are reacted with formic acid, if appropriate in the presence of hydrogen or a non-noble metal, if appropriate in the presence of a catalyst and if appropriate in the presence of a further reaction auxiliary.

If appropriate, the compounds according to the invention exist in the form of mixtures of various isomeric forms which are possible, in particular stereoisomers such as, for example, E and Z, threo and erythro, and optical isomers. We claim the E and Z isomers, the threo and erythro, and the optical isomers and also any mixtures of these.

Preferred is the use of the compounds, or preferred are the new compounds, of the formula (I) in which A represents a single linkage or an alkylene chain having 1 to 6 carbon atoms, $R^1$ represents hydrogen, alkyl or alkoxy, each of which has 1 to 4 carbon atoms, $R^2$ represents cycloalkyl or cycloalkenyl, each of which has 3 to 12 carbon atoms and each of which is optionally monosubstituted or polysubstituted by identical or different substituents from the series consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl;

or represents aryl having 3 to 12 ring members or heterocyclyl having 3 to 8 ring members, it being possible for each of these aryl or heterocyclyl substituents to be optionally monosubstituted or polysubstituted by identical or different substituents, the possible substituents preferably being selected from the enumeration which follows:

halogen, cyano, amino, hydroxyl, formyl, carboxyl, carbamoyl, thiocarbamoyl, in each case straight-chain or branched alkyl, alkoxy, alkylthio, alkylsulphinyl or alkylsulphonyl, each of which as 1 to 6 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy, each of which has 2 to 6 carbon atoms and 1 to 13 identical or different halogen atoms;

in each case straight-chain or branched acylamino, N-acyl-N-alkylamino, alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties;

in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, aryloxyalkyl, arylthioalkyl, heterocyclyl, heterocyclyloxy, heterocyclylthio, heterocyclylalkyl, heterocyclylalkyloxy or heterocyclylalkylthio, each of which is optionally monosubstituted or polysubstituted by identical or different substituents from the series consisting of halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl, each of which has 1 to 6 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy, each of which has 2 to 6 carbon atoms and 1 to 13 identical or different halogen atoms;

in each case straight-chain or branched acylamino, N-acyl-N-alkylamino, alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties;

in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms.

In particular, the invention relates to the use of the compounds, or to the new compounds, of the formula (I) in which A represents a single linkage, or methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), $R^1$ represents hydrogen, methyl, ethyl, n- or i-propyl, n-, i-, s- or t-butyl, methoxy, ethoxy, n- or i-propoxy, $R^2$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to hexasubstituted by fluorine, chlorine, bromine, cyano, carboxyl, methyl, ethyl, methoxy, ethoxy, n- or i-propyl, methoxy-carbonyl or ethoxy-carbonyl;

or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the enumeration which follows:

fluorine, chlorine, bromine, cyano, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted to tetrasubstituted by identical or different substituents from the series consisting of fluorine, chlorine, methyl, trifluoromethyl, ethyl and n- or i-propyl, cyclopropyl, cyclobutyl, cyclopentyl or cyclohexyl, and/or phenyl, phenoxy, phenylalkyl, phenylthio, phenoxyalkyl, phenylthioalkyl, phenylalkyloxy or phenylalkylthio, each of which has 1 to 4 carbon atoms in the respective alkyl chains and each of which is optionally monosubstituted to tetrasubstituted by identical or different substituents from the series consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl, and cyclopropyl, cyclobutyl, cyclopentyl or cyclohexyl.

Particularly preferred is the use of the compounds, or are the new compounds, of the formula (1) in which A represents a single linkage or methylene, 1,1-ethylene, 1,2-ethylene, 1,1-, 1,2-, 1,3- or 2,2-propylene, 1,1-, 1,2-, 1,3-, 1,4-, 2,2-, 2,i-butylene or 1,1-, 1,2- or 1,3-(2-methyl-propylene), $R^1$ represents hydrogen, methyl, ethyl, methoxy or ethoxy, $R^2$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to hexasubstituted by fluorine, chlorine, bromine, cyano, carboxyl, methyl, ethyl, methoxy, ethoxy, n- or i-propyl, methoxy-carbonyl or ethoxy-carbonyl;

or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the enumeration which follows:

fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted to tetrasubstituted by identical or different substituents from the series consisting of fluorine, chlorine, methyl, trifluoromethyl, ethyl and n- or i-propyl, cyclopropyl, cyclobutyl, cyclopentyl or cyclohexyl, and/or phenyl, phenoxy, phenylthio, benzyl, phenylethyl, phenylpropyl, benzyloxy, benzylthio, phenoxymethyl, phenoxyethyl, phenylthiomethyl or phenylthioethyl, each of which is optionally monosubstituted to tetrasubstituted by identical or different substituents from the series consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl, and cyclopropyl, cyclobutyl, cyclopentyl or cyclohexyl.

Very particularly preferred is the use of the compounds, or are new compounds, of the formula (1) in which A represents a single linkage or methylene, 1,1-ethylene, 1,2-ethylene, 1,1-propylene, 1,2-propylene or 2,2-propylene, $R^1$ represents hydrogen, $R^2$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted or disubstituted by methyl, ethyl, methoxy or ethoxy;

or represents in each case optionally monosubstituted to trisubstituted phenyl, naphthyl, furyl, benzofuranyl, pyrrolyl, indolyl, thienyl, benzothienyl, pyridyl, quinolyl, pyrimidyl, pyridazinyl or pyrazinyl, and the possible substituents preferably being selected from the enumeration which follows:

fluorine, chlorine, bromine, cyano, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetyl amino, formylamino, N-formyl-N-methyl amino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted to tetrasubstituted by identical or different substituents from the series consisting of fluorine, chlorine, methyl, trifluoromethyl, ethyl and n- or i-propyl, and/or phenyl, phenoxy, phenylthio, benzyl, phenyl-1-ethyl, phenyl-2-ethyl, benzyloxy, benzylthio, phenoxymethyl or phenylthiomethyl, each of which is optionally monosubstituted to tetrasubstituted by identical or different substituents from the series consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoroethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methlylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, and in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl.

The abovementioned definitions of radicals of which general or preferred ranges have been given apply to the end products of the formula (I) and analogously for the starting materials or intermediates required in each case for the preparation.

These definitions of radicals can be combined with each other as desired, that is to say combinations between the ranges given of preferred compounds are also possible.

Formula (II) provides a general definition of the aminosalicylamides required as starting materials for carrying out process a). In this formula (II), A and $R^2$ preferably, or in particular, have those meanings which have already been mentioned in connection with the description of the compounds of the formula (I) according to the invention, as being preferred, or particularly preferred, for A and $R^2$.

With the exception of 4-{4-[(3-amino-2-hydroxybenzoyl)-amino]-3-hydroxy-1-piperidyl}-N,N,4-trimethyl-2,2-diphenylbutanamide, the starting materials of the formula (II) are new and also part of the present application.

The aminosalicylamides of the formula (II) are obtained when (process a-1a) nitrosalicylamides of the general formula (IV)

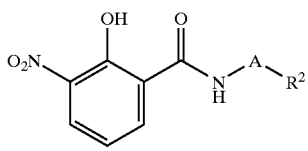
(IV)

in which
  A and $R^2$ have the abovementioned meanings
  are reacted with hydrogen, if appropriate in the presence of a diluent, preferably an ester such as methyl acetate or ethyl acetate; an alcohol such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether; water, a salt solution such as, for example, ammonium chloride solution, an acid such as, for example, hydrochloric acid or acetic acid, and any mixtures of the abovementioned diluents, and, if appropriate, in the presence of a catalyst such as, for example, Raney nickel, palladium or platinum, if appropriate on a carrier material such as active charcoal,
  or when (process a-1b) O-benzyl-nitrosalicylamide of the general formula (V)

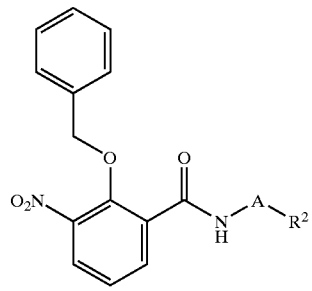
(V)

in which
  A and $R^2$ have the abovementioned meanings
  are reacted with hydrogen, if appropriate in the presence of a diluent, preferably an ester such as methyl acetate or ethyl acetate, an alcohol such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether; an acid such as, for example, acetic acid; water; and any mixtures of the abovementioned diluents, and, if appropriate, in the presence of a catalyst such as, for example, Raney nickel, palladium or platinum, if appropriate on a carrier material such as, for example, active charcoal.

The nitrosalicylamides of the formula (IV) required as starting materials for carrying out process a-1a) according to the invention are described further below in connection with the description of process b) according to the invention.

Formula (V) provides a general definition of the O-benzyl-nitrosalicylamides required as starting materials for carrying out process a-1b) according to the invention. In this formula (V), A and $R^2$ preferably, or in particular, have those meanings which have already been mentioned in connection with the description of the compounds of the formula (I) according to the invention as being preferred, or particularly preferred, for A and $R^2$.

The O-benzyl-nitrosalicylamides of the formula (V) were hitherto unknown and, being new substances, form part of the present application.

The O-benzyl-nitrosalicylamides of the formula (V) are obtained when (process a-2) O-benzyl-nitrosalicylic acid derivatives of the formula (VI)

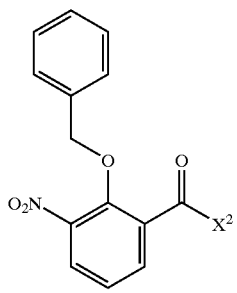
(VI)

in which
  $X^2$ represents halogen, hydroxyl or alkoxy
  are reacted with an amine of the formula (VII)

(VII)

in which
  A and $R^2$ have the abovementioned meanings,
  if appropriate in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, tetrachloromethane, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone such as acetone, butanone, methyl isobutyl ketone or cyclohexanone; a nitrile such as acetonitrile, propionitrile, n- or i-butyronitrile or benzonitrile; an amide such as N,N-dimethylformamide, N,N-dimethylacetamide, N-methylformanilide, N-methylpyrrolidone or hexamethylphosphoric triamide; an ester such as methyl acetate or ethyl acetate; a sulphoxide such as dimethyl sulphoxide; or a sulphone such as sulfolane, if appropriate in the presence of a condensing agent, for example an acid halide former such as phosgene, phosphorus tribromide, phosphorus trichloride, phosphorus pentachloride, phosphorus oxychloride or thionyl chloride; an anhydride former such as ethyl chloroformate, methyl chloroformate, isopropyl chloroformate, isobutyl chloroformate or methanesulphonyl chloride; a carbodiimide such as N,N'-dicylcohexylcarbodiimide (DCC), or another customary condensing agent such as phosphorus pentoxide, polyphosphoric acid, N,N'- carbonyldiimidazole, 2-ethoxy-N-ethoxy-carbonyl-1,2-dihydroquinoline (EEDQ) or triphenylphosphine/carbon tetrachloride and, if appropriate, in the presence of an acid acceptor, preferably an alkaline earth metal hydride, hydroxide, amide, alcoholate, acetate, carbonate, hydrogen carbonate or an alkali metal hydride, hydroxide, amide, alcoholate, acetate, carbonate or hydrogen carbonate such as, for example, sodium hydride, sodium amide, sodium methylate, sodium ethylate, potassium . tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, or a tertiary amine such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Formula (VI) provides a general definition of the O-benzyl-nitrosalicylic acid derivatives required as starting materials for carrying out process a-2) according to the invention. In this formula (VI), $X^2$ represents halogen, preferably chlorine, hydroxyl or alkoxy, preferably methoxy or ethoxy.

The O-benzyl-nitrosalicylic acid derivatives of the formula (VI) are known and can be prepared by known methods (compare, for example, J. Am. Chem. Soc. 1959, 5215–5217).

Formula (VII) provides a general definition of the amines furthermore required as starting materials for carrying out process a-2) according to the invention. In this formula (VII), A and $R^2$ preferably, or in particular, have those meanings which have already been given in connection with the description of the compounds of the formula (I) according to the invention as being preferred, or particularly preferred, for A and $R^2$.

The amines of the formula (VII) are known reagents in organic chemistry.

Formula (III) provides a general definition of the acylating agents furthermore required as starting materials for carrying out process a) according to the invention. In this formula (III), $R^1$ preferably, or in particular, has the meaning which has already been mentioned in connection with the description of the compounds of the formula (I) according to the invention as being preferred, or particularly preferred, for $R^1$. $X^1$ represents halogen, hydroxyl, alkoxy or alkylcarbonyloxy, preferably chlorine, hydroxyl, methoxy, ethoxy or acetoxy.

The acylating agents of the general formula (III) are known reagents in organic chemistry.

Formula (IV) provides a general definition of the nitrosalicylamides required as starting materials for carrying out process b) according to the invention. In this formula (IV), A and $R^2$ preferably, or in particular, have those meanings which have already been given in connection with the description of the compounds of the formula (I) according to the invention as being preferred, or particularly preferred, for A and $R^2$.

The nitrosalicylamides of the formula (IV) are known in some cases and/or can be prepared by known methods (compare, for example, Arzneim-Forsch (1978), 28(9), 1550–3).

New, and also part of the present application, are nitrosalicylamides of the formula (IV-a)

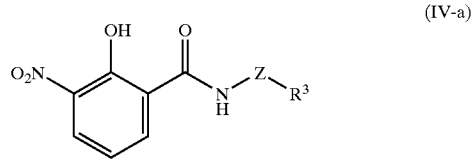

in which

Z represents a single linkage or an alkylene chain and $R^3$ represents in each case optionally mono- to trisubstituted cycloalkyl, cycloalkenyl, aryl or heteroaryl having up to 3 hetero atoms, with the exception of the nitro group as substituent, and the compounds N-[3-chloro-4-(4-chlorophenoxy)phenyl]-2-hydroxy-3-nitro-benzamide,
N-(4-decylphenyl)-2-hydroxy-3-nitro-benzamide,
N-(3,4-dimethylphenyl)-2-hydroxy-3-nitro-benzamide,
3-nitro-N-phenethyl-salicylamide,
N-benzyl-3-nitro-salicylamide,
N-(4-aminophenyl)-2-hydroxy-3-nitro-benzamide,
N-(2-chloro-6-methylphenyl)-2-hydroxy-3-nitro-benzamide,
N-(3-chloro-2-methylphenyl)-2-hydroxy-3-nitro-benzamide,
2-hydroxy-3-nitro-N-(2,4,6-trichlorophenyl)-benzamide,
N-(2,3-dimethylphenyl)-2-hydroxy-3-nitro-benzamide,
N-(2-ethylphenyl)-2-hydroxy-3-nitro-benzamide,
2-hydroxy-3-nitro-N-phenyl-benzamide,
2-hydroxy-N-(4-methylphenyl)-3-nitro-benzamide,
2-hydroxy-N-(2-methylphenyl)-3-nitro-benzamide,
2-hydroxy-N-(4-methoxyphenyl)-3-nitro-benzamide,
2-hydroxy-N-(2-methoxyphenyl)-3-nitro-benzamide,
2-hydroxy-N-(2-hydroxyphenyl)-3-nitro-benzamide,
2-hydroxy-N-(2-hydroxyphenyl)-3-nitro-benzamides,
2-[(2-hydroxy-3-nitrobenzoyl)amino]-benzoic acid,
N-(2,6-dimethylphenyl)-2-hydroxy-3-nitro-benzamide,
N-(2,5-dimethylphenyl)-2-hydroxy-3-nitro-benzamide,
2-hydroxy-3-nitro-N-[2-phenoxy-5-(trifluoromethyl)phenyl]-benzamide,
N-[2-chloro-5-(trifluoromethyl)phenyl]-2-hydroxy-3-nitro-benzamide,
2-hydroxy-3-nitro-N-[4-(phenylazo)phenyl]-benzamide,
N-(2,4-dimethylphenyl)-2-hydroxy-3-nitro-benzamide,
N-(5-chloro-2-methoxyphenyl)-2-hydroxy-3-nitro-benzamide,
N-(4-chloro-2-methylphenyl)-2-hydroxy-3-nitro-benzamide,
N-(2-chloro-4-methylphenyl)-2-hydroxy-3-nitro-benzamide,
N-(4-bromo-2-methylphenyl)-2-hydroxy-3-nitro-benzamide,
N-(4-chloro-2,5-dimethoxyphenyl)-2-hydroxy-3-nitro-benzamide,
N-(2,5-dibromophenyl)-2-hydroxy-3-nitro-benzamide,
N-(2-fluorophenyl)-2-hydroxy-3-nitro-benzamide,
N-(3-fluorophenyl)-2-hydroxy-3-nitro-benzamide,
2-hydroxy-N-(2-iodophenyl)-3-nitro-benzamide,
2-hydroxy-N-(3-iodophenyl)-3-nitro-benzamide,
N-(2-bromophenyl)-2-hydroxy-3-nitro-benzamide,
N-(3-bromophenyl)-2-hydroxy-3-nitro-benzamide,
N-(2,5-dichlorophenyl)-2-hydroxy-3-nitro-benzamide, N-(3,4-dichlorophenyl)-2-hydroxy-3-nitro-benzamide,
2',3',5'-trichloro-6'-hydroxy-3-nitro-salicylanilide,
N-(p-hydroxy-a-methylphenethyl)-3-nitro-salicylamide,
3-nitro-3',5'-bis(trifluoromethoxy)-salicylanilide,
N-(2,4-dichlorophenyl)-2-hydroxy-3-nitro-benzamide,
2-hydroxy-N-(4-iodophenyl)-3-nitro-benzamide,
N-(4-bromophenyl)-2-hydroxy-3-nitro-benzamide,
N-(2-chlorophenyl )-2-hydroxy-3-nitro-benzamide,
N-(3-chlorophenyl)-2-hydroxy-3-nitro-benzamide,
N-(4-chlorophenyl)-2-hydroxy-3-nitro-benzamide and
N-(4-fluorophenyl)-2-hydroxy-3-nitro-benzamide are accepted.

The nitrosalicylamides of the formula (IV-a) are obtained, process b-1), when 2-hydroxy-3-nitrobenzoic acid or 2-hydroxy-3-nitrobenzoyl chloride is reacted with an amine of the formula (VIII)

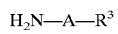

$$H_2N—A—R^3 \qquad (VIII)$$

in which

A and $R^3$ have the abovementioned meanings, if appropriate in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, tetrachloromethane, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisol; a ketone such as acetone, butanone, methyl isobutyl ketone or cyclohexanone; a nitrile such as acetonitrile, propionitrile, n- or i-butyronitrile or benzonitrile; an amide such as N,N-dimethylformamide, N,N-dimethylacetamide, N-methylformanilide, N-methylpyrrolidone or hexamethylphosphoric triamide; an ester such as methyl acetate or ethyl acetate; a sulphoxide such as dimethyl sulphoxide; or a sulphone such as sulpholane, if appropriate in the presence of a condensing agent, for example an acid halide former such as phosgene, phosphorus tribromide, phosphorus trichloride, phosphorus pentachloride, phosphorus oxychloride or thionyl chloride; an anhydride former such as ethyl chloroformate, methyl chloroformate, propyl chloroformate, isobutyl chloroformate or methanesulphonyl chloride; a carbodiimide such as N,N'-dicyclohexylcarbodiimide (DCC), or another customary condensing agent such as phosphorus pentoxide, polyphosphoric acid, N,N'-carbonyldiimidazole, 2-ethoxy-N-ethoxycarbonyl-1,2-dihydroquinoline (EEDQ) or triphenylphosphine/carbon tetrachloride, and, if appropriate, in the presence of an acid acceptor, preferably a hydride, hydroxide, amide, alcoholate, acetate, carbonate or hydrogen carbonate of an alkaline earth metal or alkali metal such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, or a tertiary amine such as trimethylamine, triethylamine, tributylamine, N,N-dimethylaniline, N,N-dimethylbenzylamine, pyridine, N-methylpiperidine N-methylmorpholine, N,N-dimethylaminopyridine, diazabicyclooctane (DABCO), diazabicyclononene (DBN) or diazabicycloundecene (DBU).

Furthermore, it has been found that the new nitrosalicylamides of the formula (IV-a) are suitable for controlling pests on plants and industrial materials, preferably fungi, insects and bacteria.

Formula (IV-a) provides a general definition of the new nitrosalicylamides. Preferred new compounds of the formula (IV-a) are those in which Z represents a single linkage or an alkylene chain having 1 to 6 carbon atoms, $R^3$ represents cycloalkyl or cycloalkenyl, each of which has 3 to 12 carbon atoms and each of which is optionally mono- to trisubstituted by identical or different substituents from the series consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl;

or represents aryl having 3 to 12 ring members or heterocyclyl having 3 to 8 ring members, it being possible for each of these aryl or heterocyclyl substituents to be mono- to trisubstituted by identical or different substituents, the possible substituents preferably being selected from the enumeration which follows:

halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl, each of which has 1 to 6 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy, each of which has 2 to 6 carbon atoms and 1 to 13 identical or different halogen atoms;

in each case straight-chain or branched acylamino, N-acyl-N-alkylamino, alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties;

in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, aryloxyalkyl, arylthioalkyl, heterocyclyl, heterocyclyloxy, heterocyclylthio, heterocyclylalkyl, heterocyclylalkyloxy or heterocyclylalkylthio, each of which is optionally monosubstituted or polysubstituted by identical or different substituents from the series consisting of halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl, each of which has 1 to 6 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy, each of which has 2 to 6 carbon atoms and 1 to 13 identical or different halogen atoms;

in each case straight-chain or branched acylamino, N-acyl-N-alkylamino, alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties;

in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms.

In particular, the invention relates to the new nitrosalicylamides of the formula (IV-a) in which A represents a single linkage, or methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), $R^1$ represents hydrogen, methyl, ethyl, n- or i-propyl, n-, i-, s- or t-butyl, methoxy, ethoxy, n- or i-propoxy, $R^3$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to trisubstituted by fluorine, chlorine, bromine, cyano, carboxyl, methyl, ethyl, methoxy, ethoxy, n- or i-propyl, methoxy-carbonyl or ethoxy-carbonyl;

or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the enumeration which follows:

fluorine, chlorine, bromine, cyano, amino, hydroxyl, formyl, carboxyl, carbamoyl, thiocarbamoyl, methyl, ethyl, n- or 1-propyl, n-, i-, s- or t-butyl, methoxy, ethoxy, n- or i-propoxy, methylthio, ethylthio; n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted to tetrasubstituted by identical or different substituents from the series consisting of fluorine, chlorine, methyl, trifluoromethyl, ethyl and n- or i-propyl, cyclopropyl, cyclobutyl, cyclopentyl or cyclohexyl, and/or phenyl, phenoxy, phenylalkyl, phenylthio, phenoxyalkyl, phenylthioalkyl, phenylalkyloxy or phenylalkylthio, each of which has 1 to 4 carbon atoms in the respective alkyl chains and each of which is optionally monosubstituted to tetrasubstituted by identical or different substituents from the series consisting of fluorine, chlorine, bromine, cyano, formyl, carbamoyl, thiocarbamoyl, methyl, ethyl, n- or 1-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or 1-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl, and cyclopropyl, cyclobutyl, cyclopentyl or cyclohexyl.

Particularly preferred are the new nitrosalicylamides of the formula (IV-a) in which A represents a single linkage or methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), R1 represents hydrogen, methyl, ethyl, methoxy or ethoxy, $R^3$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to trisubstituted by fluorine, chlorine, bromine, cyano, carboxyl, methyl, ethyl, methoxy, ethoxy, n- or i-propyl, methoxy-carbonyl or ethoxy-carbonyl;

or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the enumeration which follows:

fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted to tetrasubstituted by identical or different substituents from the series consisting of fluorine, chlorine, methyl, trifluoromethyl, ethyl and n- or i-propyl, cyclopropyl, cyclobutyl, cyclopentyl or cyclohexyl, and/or phenyl, phenoxy, phenylthio, benzyl, phenylethyl, phenylpropyl, benzyloxy, benzylthio, phenoxymethyl, phenoxyethyl, phenylthiomethyl or phenylthioethyl, each of which is optionally monosubstituted to tetrasubstituted by identical or different substituents from the series consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl, and cyclopropyl, cyclobutyl, cyclopentyl or cyclohexyl.

Very particularly preferred are the new nitrosalicylamides of the formula (IV-a) in which A represents a single linkage or methylene, 1,1-ethylene, 1,2-ethylene, 1,1-propylene, 1,2-propylene or 2,2-propylene, $R^1$ represents hydrogen, $R^3$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted or disubstituted by methyl, ethyl, methoxy or ethoxy;

or represents in each case optionally monosubstituted to trisubstituted phenyl, naphthyl, furyl, benzofuranyl, pyrrolyl, indolyl, thienyl, benzothienyl, pyridyl, quinolyl, pyrimidyl, pyridazinyl or pyrazinyl, and the possible substituents preferably being selected from the enumeration which follows:

fluorine, chlorine, bromine, cyano, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted to tetrasubstituted by identical or different substituents from the series consisting of fluorine, chlorine, methyl, trifluoromethyl, ethyl and n- or i-propyl, and/or phenyl, phenoxy, phenylthio, benzyl, phenyl-1-ethyl, phenyl-2-ethyl, benzyloxy, benzylthio, phenoxymethyl or phenylthiomethyl, each of which is optionally monosubstituted to tetrasubstituted by identical or different substituents from the series consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, and in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl.

2-Hydroxy-3-nitrobenzoic acid or 2-hydroxy-3-nitrobenzoyl chloride, which are required are starting materials for carrying out process b-1), are known (compare, for example, J. Chem. Soc., 1953 2049, 2050 or U.S. Pat. No. 3,527,865).

Formula (VIII) provides a general definition of the amines furthermore required as starting materials for carrying out process b-1) according to the invention. In this formula (VIII) A and $R^3$ preferably, or in particular, have the meanings which have already been described further above in connection with the compounds of the formula (IV-a) according to the invention as being preferred, or particularly preferred, for A and $R^3$.

The amines of the formula (VIII) are known reagents in organic chemistry.

The O-benzyl-nitrosalicylamides of the formula (V) which are required as starting materials for carrying out process c) according to the invention have already been described further above in connection with the description of process a-1b) according to the invention.

Diluents which are suitable for carrying out process a) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, or sulphones such as sulfolane.

If appropriate, process (a) according to the invention is carried out in the presence of a suitable acid acceptor. Suitable acid acceptors are all customary inorganic or organic bases. These preferably include alkaline earth metal hydroxides, acetates, carbonates or hydrogen carbonates and alkali metal hydroxides, acetates, carbonates or hydrogen carbonates such as, for example, sodium hydroxide, potassium hydroxide, sodium acetate, potassium acetate, calcium acetate, sodium carbonate, potassium carbonate, potassium hydrogen carbonate or sodium hydrogen carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

If appropriate, processes b) and c) according to the invention are carried out in the presence of a catalyst. Suitable catalysts are all those which are also generally used for hydrogenation reactions. The following may be mentioned as examples: Raney nickel, palladium or platinum, if appropriate on a support such as, for example, active charcoal.

If appropriate, process c) according to the invention is also carried out in the presence of hydrogen or, if appropriate, in the presence of a non-noble metal. Examples of non-noble metals which may be mentioned are: zinc, tin, iron, aluminium or magnesium.

Other reaction auxiliaries which are suitable for carrying out processes a), b) and c) according to the invention are all dehydrating agents, in particular acetic anhydrides.

When carrying out processes a), b) and c) according to the invention, the reaction temperatures can be varied within a substantial range. In general, the processes are carried out at temperatures from 0° C. to 180° C., preferably at temperatures from 0° C. to 130° C.

To carry out process a) according to the invention for the preparation of the compounds of the formula (I), 1 to 2000 mol, preferably 1 to 800 mol, of acylating agent of the formula (III) are generally employed per mol of the aminosalicylamide of the formula (II).

To carry out processes b) and c) according to the invention for the preparation of the compounds of the formula (I), 100 to 2000 mol, preferably 200 to 1000 mol, of formic acid are generally employed per mol of the nitrosalicylamide of the formula (IV) or of the O-benzyl-nitrosalicylamide of the formula (V), respectively.

Processes a), b) and c) according to the invention are generally carried out at atmospheric pressure. However, they can also be carried out under elevated or reduced pressure, in general between 0.1 bar and 10 bar.

The active compounds according to the invention have a powerful microbicidal activity and can be employed under practice conditions for controlling undesirable microorganisms. The active compounds are suitable for use as crop protection products, in particular as fungicides.

Fungicidal agents are employed in crop protection for controlling Plasmodiophoromycetes, Oomycetes, Chytridiomycetes, Zygomycetes, Ascomycetes, Basidiomycetes and Deuteromycetes.

Bactericidal agents are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example; *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The fact that the active compounds are well tolerated by plants at the concentrations required for controlling plant diseases permits the treament of aerial parts of plants, of propagation stock and seeds, and of the soil.

The active compounds according to the invention are employed particularly successfully for controlling diseases in viticulture and fruit and vegetable growing such as, for example, against Sphaerotheca and Venturia species, for controlling cereal diseases such as, for example, against Pseudocercosporella species, or for controlling rice diseases, such as, for example, against *Pyricularia oryzae.* Other cereal diseases such as Septoria, Cochliobolus and Pyrenophora species are also controlled successfully. Other diseases in viticulture and fruit and vegetable growing, such as Phytophthora, Plasmopara, Podosphaera and Botrytis, are also controlled successfully.

Depending on their particular physical and/or chemical properties, the active compounds can be converted into the customary formulations, such as solutions, emulsions, suspensions, powders, foams, pastes, granules, aerosols, microencapsulations in polymeric substances and in coating compositions for seed, as well as ULV cold and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylene or methylene chloride, aliphatic hydrocarbons such as cyclohexane or paraffins, for example mineral oil fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, as well as water. Liquefied gaseous extenders or carriers are to be understood as meaning liquids which are gaseous at ambient temperature and under atmospheric pressure, for example aerosol propellants such as halogenated hydrocarbons as well as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly-disperse silica, alumina or silicates. Suitable solid carriers for granules are: for example crushed and fractionated natural rocks such as calcite, marble, pumice, sepiolite and dolomite, synthetic (granules of inorganic and organic meals, and granules of organic material such as sawdust, coconut shells, maize cobs and tobacco stalks. Suitable emulsifiers and/or foam-forming agents are: for example non-ionic and anionic emulsifiers such as polyoxyethylene fatty acid esters, polyoxyethylenefatty alcohol ethers, for example alkylaryl polyglycol ethers, alkylsulphonates, alkyl sulphates, arylsulphonates as well as protein hydrolysates. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in their formulations, can also be used as a mixture with known fungicides, bactericides, acaricides, nematicides or insecticides, for example to widen the spectrum of action or to prevent the build-up of resistance. In many cases, synergistic effects are obtained, i.e. the activity of the mixture is greater than the activity of the individual components.

Examples of suitable components in mixtures are the following compounds:

Fungicides aldimorph, ampropylfos, ampropylfos-potassium, andoprim, anilazine, azaconazole, azoxystrobin, benalaxyl, benodanil, benomyl, benzamacril, benzamacrylisobutyl, bialaphos, binapacryl, biphenyl, bitertanol, blasticdiin-S, bromuconazole, bupirimate, buthiobate, calcium polysulphide, capsimycin, captafol, captan, carbendazim, carboxin, carvon, quinomethionate, chlobenthiazon, chlorfenazole, chloroneb, chloropicrin, chlorothalonil, chlozolinate, clozylacon, cufraneb, cymoxanil, cyproconazol, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzon, fluazinam, flumetover, fluoromid, fluquinconazole, flurprimidol, flusilazol. flusulfamid, flutolanil, flutriafol, folpet, fosetyl-alminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazol, imazalil, imibenconazole, iminoctadine, iminoctadinealbesilate, iminoctadinetriacetate, iodocarb, ipconazole, iprobenfosufen (IBP), iprodione, irumamycin, isoprothiolan, isovaledione, kasugamycin, kresoxim-methyl, copper preparations such as copper hydroxide, copper naphthenate, copper oxychloride, copper sulphate, copper oxide, oxine-copper and Boerdeaux mixture, mancopper, mancozeb, maneb, merferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinicacid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozcene(PCNB), sulphur and sulphur preparations, tebuconazole, tecloftalam, tecnhazene, tetcyclacis, tetraconazole, thiabendazole, thicyofen, thifluzamide, tthiophanate-methyl, thiram, tioxymid, tolclofos-methyl, tolylfluanid, triadimefon, triadimenol, triazbutanil, triazoxide, trichlamide, tricyclazole, tridemorph, triflumizole, triforine, triticonazole, uniconazole, validamycin A, vinclozolin, viniconazole, zarilamid, zineb, ziram, and also Dagger G.

OK-8705,

OK-8801,

2',6'-dibromo-2-methyl-4'-trifluoromethoxy-4'-trifluoro-methyl-1,3-thiazole-5-carboxanilide, 2,6-dichloro-N-(4-trifluoromethylbenzyl)-benzamide, 2-aminobutane, 2-phenylphenol(OPP), 8-hydroxyquinoline sulphate, cis-1-(4-chlorophenyl)-2-(1H-1,2,4-triazol-1-yl)-cycloheptanol, (5RS,6RS)-6-hydroxy-2,2,7,7-tetramethyl-5-(1H-1,2,4-triazol-1-yl)-3-octanone, α-(2,4-dichlorophenyl)-β-methoxy-α-methyl-1H-1,2,4-triazole-1-ethanol, α-(1,1-dimethylethyl)-β-(2-phenoxyethyl)-1H-1,2,4-triazole-1-ethanol, 1-[1-[2-[(2,4-dichlorophenyl)methoxy]phenyl]ethenyl]-1H-imidazole, bis-(1-methylethyl)-3-methyl-4-[(3-methylbenzoyl)oxy]-2,5-thiophene dicarboxylate, 2,6-dichloro-N-[[4-(trifluoromethyl)phenyl]methyl]-benzamide, (E)-α-(methoxyimino)-N-methyl-2-phenoxy-phenylacetamide, 9H-xanthene-9-carbo-2-[(phenylamino)-carbonyl]-hydrazide, O-methyl S-phenyl phenylpropylphosphoramidothioate, N-(5-chloro-2-methylphenyl)-2-methoxy-N-(2-oxo-3-oxazolidinyl)-acetamide, 1-(2,4-dichlorophenyl)-2-(1H-1,2,4-triazol-1-yl)ethanone O-(phenylmethyl)-oxime, N-(2,6-dimethylphenyl)-2-methoxy-N-(tetrahydro-2-oxo-3-thienyl)-acetamide, cis-4-[3-[4-(1,1-dimethylpropyl)-phenyl-2-methylpropyl]-2,6-dimethyl-morpholine hydrochloride, α-(2,4-dichlorophenyl)-β-fluoro-β-propyl-1H-1,2,4-triazole-1-ethanol, 3-(1,1-dimethylpropyl)-1-oxo-1H-indene-2-carbonitrile, 2,6-dichloro-5-(methylthio)-4-pyrimidinyl thiocyanate, S-methyl-1,2,3-benzothiadiazole-7-carbothioate, N-(6-methoxy)-3-pyridinyl)-cyclopropanecarboxamide, 3,5-dichloro-N-[cyano[(1-methyl-2-propynyl)oxy]methyl]-benzamide, 4-chloro-2-cyano-N,N-dimethyl-5-(4-methylphenyl)-1H-imidazole-1-sulphonamide, 8-(1,1-dimethylethyl)-N-ethyl-N-propyl-1,4-dioxaspiro[4,5]decane-2-methaneamine, 2,2-dichloro-N-[1-(4-chlorophenyl)ethyl]-1-ethyl-3-methyl-cyclopropanecarboxamide, N-(2,3-dichloro-4-hydroxyphenyl)-1-methyl-cyclohexanecarboxamide.

1-(3,5-dichlorophenyl)-3-(2-propenyl)-2,5-pyrrolidinedione, 1-methyl-5-nonyl-2-(phenylmethyl)-3-pyrrolidinole, 1-[[2-(4-chlorophenyl)-3-phenyloxiranyl]-methyl]-1H-1,2,4-triazole, methanetetrathiol, sodium salt, 2-(2,3,3-triiodo-2-propenyl)-2H-tetrazole, N-[3-chloro-4,5-bis(2-propinyloxy)-phenyl]-N'-methoxy-methanemidamide, α-(5-methyl-1,3-dioxan-5-yl)-β-[[4-(trifluoromethyl)-phenyl]-methylene]-1H-1,2,4-triazole-1-ethanol, 1-(2-methyl-1-naphthalenyl)-1H-pyrrole-2,5-dione, N-(2,6-dimethylphenyl)-2-methoxy-N-(tetrahydro-2-oxo-3-furanyl)-acetamide, 3,4-dichloro-1-[4-(difluoromethoxy)-phenyl]1H-pyrrole-2,5-dione, N-[2,2,2-trichloro-1-[(chloroacetyl)-amino]-ethyl]-benzamide, N-formyl-N-hydroxy-DL-alanine, monosodium salt, N-(4-cyclohexylphenyl)-1,4,5,6-tetrahydro-2-pyrimidineamine, 4-methyl-tetrazolo[1,5-a]quinazolin-5(4H)-onm,2-chloro-N-(2,6-dimethylphenyl)-N-(isothiocyanatomethyl)-acetamide, ethyl [(4-chlorophenyl)-azo]-cyanoacetate, N-(4-hexylphenyl)-1,4,5,6-tetrahydro-2-pyrimidineamine, N-(2-chloro-4-nitrophenyl)-4-methyl-3-nitro-benzenesulphonamide, methyl N-(chloroacetyl)-N-(2,6-dimethylphenyl)-DL-alaninate, 3-[2-(4-chlorophenyl)-5-ethoxy-3-isoxazolidinyl]-pyridine,
[2-methyl-1-[[[1-(4-methyl)ethyl]amino]carbonyl]-propyl] carbaminic-acid-1-methylethylester,
2-[(1-methylethyl)sulphonyl]-5-(trichloromethyl)-1,3,4-thiadiazole,
spiro[2H]-1-benzopyran-2,1'(3'H)-isobenzofuran]-3'-one,
methyl N-(2,6-dimethylphenyl)-N-(5-isoxazolylcarbonyl)-DL-alaninate,
potassium hydrogen carbonate,
1-[[2-(2,4-dichlorophenyl)-1,3-dioxolan-2-yl]-methyl]-1H-imidazole,
1-[(diiodomethyl)-sulphonyl]-4-methyl-benzene,
2-bromo-2-(bromomethyl)-glutaronitrile,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
methyl 1-(2,3-dihydro-2,2-dimethyl-1H-inden-1-yl)-1H-imidazole-5-carboxylate,
2-chloro-N-(2,3-dihydro-1,1,3-trimethyl-1H-inden-4-yl)-3-pyridinecarboxamide,
O,O-diethyl [2-(dipropylamino)-2-oxoethyl]-ethylphosphoramidothioate, A mixture with other known active compounds, such as herbicides, or with fertilizers and growth regulators is also possible.

The active compounds can be used as such or in the form of their commercially available formulations or the use forms prepared therefrom, such as ready-to-use solutions, suspensions, wettable powders, pastes, soluble powders, dusts and granules. They are used in the customary manner, for example by watering, spraying, atomizing, scattering, foaming, brushing on and the like. If appropriate, the active compounds are applied by the ultra-low volume method, or the active compound formulation or the active compound itself is injected into the soil. If appropriate, the seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.2% by weight, are required at the site of action.

The active compounds are well tolerated by plants, have a favourable toxicity to warm-blooded species, and are suitable for controlling animal pests, in particular insects, arachnids and nematodes, which are encountered in agriculture, in forests, in the protection of stored products and of materials, and in the hygiene field. They can preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus,* Oscinella frit, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinenma spp and Trichodorus spp.

The compounds of the formula (I) according to the invention are distinguished, in particular, by their activity against the larvae of the mustard beetle (*Phaedon cochleariae*), the caterpillars of the diamond-back moth (*Plutella maculipennis*), the caterpillars of the fall armyworm (*Spodoptera frugiperda*), and against the green rice leafhopper (*Nephotettix cincticeps*).

The active compounds can be converted into the customary formulations, such as solutions, emulsions, wettable powders, suspensions, powders, dusts, pastes, soluble powders, granules, suspension-emulsion concentrates, natural and synthetic substances impregnated with active ingredient, and microencapsulations in polymeric substances.

These formulations are produced in a known manner, for example by mixing the active compounds with extenders, that is, liquid solvents and/or solid carriers, optionally with the use of surface-active agents, that is, emulsifiers and/or dispersants, and/or foam formers.

In the case of the use of water as an extender, organic solvents can, for example, also be used as auxiliary solvents. The following are mainly suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic minerals such as highly-disperse silica, alumina and silicates, suitable solid carriers for granules are: for example crushed and fractionated natural minerals such as calcite, marble, pumice, sepiolite and dolomite, or else synthetic granules of inorganic and organic meals, and granules of organic material such as sawdust, coconut shells, maize cobs and tobacco stalks, suitable emulsifiers and/or foam formers are for example non-ionic and anionic emulsifiers such as polyoxyethtlene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyes such as alizarin dyes, azos dye and metal phthalocyanine dyes, and trace nutrients such as salts of iron, manganese, boron, copper, cobalt, molybdenum and zinc.

The formulations generally comprise between 0.1 and 95 percent by weight of active compound, preferably between 0.5 and 90%.

The active compound according to the invention can be present, in its commercially available formulations and in the use forms prepared from these formulations, as a mixture with other known active compounds, such as insecticides, attractants, sterilants, bactericides, acaricides, nematicides, fungicides, growth-regulating substances or herbicides. The insecticides include, for example, phosphoric esters, carbamates, carboxylates, chlorinated hydrocarbons, phenylureas, substances produced by mircoorganisms, and the like.

The active compounds according to the invention can furthermore be present, in their commercially available formulations and in the use forms prepared from these formulations, in the form of a mixture with synergists. Synergists are compounds by which the activity of the active compounds is increased without it being necessary for the synergist added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

They are applied in a customary manner adapted to suit the use forms.

When used against hygiene and stored-product pests, the active compound is distinguished by an outstanding residual action on wood and clay and by a good stability to alkali on limed substrates.

The active compounds according to the invention are not only active against plant, hygiene and stored-product pests, but also, in the veterinary medicine sector, against animal parasites (ectoparasites), such as hard ticks, soft ticks, mange mites, trombidae, flys (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chyrsomyia spp., Wohlfahrtia spp., Sarcophaga spp., Oestrus spp., Hypoderma spp., Gasterophilus spp., Hippobosca spp., Lipoptena spp., Helophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica,* Supella spp.

From the sub-class of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp., Varroa spp.

From the order of the Actinedida (Prostigmata) and Acaridida (Astigmata), for example, Acarapis spp., Chyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals, such as, for example, hamsters, guinea pigs, rats and mice. Controlling these arthropods is intended to reduce deaths and reduced performances (in meat, milk, wool, hides, eggs, honey and the like), so that more economical and simpler animal keeping is possible by using the active compounds according to the Invention.

In the veterinary sector, the active compounds according to the invention are used in a known manner by enteral administration in the form of, for example, tablets, capsules, drinks, drenches, granules, pastes, boli, by means of the feed-through method, via suppositories, by means of parenteral administration such as, for example, by means of injections (intramuscular, subcutaneous, intravenous, intraperitonal and the like), implants, by nasal application, by dermal administration in the form of, for example, bathing or dipping, spraying, pouring-on and spotting-on, washing, dusting, and with the aid of active-compound-comprising, shaped articles, such as collars, ear tags, tail tags, limb bands, halters, marking devices and the like.

When using for cattle, poultry, domestic animals and the like, the active compounds of the formula (I), in the form of formulations (for example powders, emulsions, flowables) which comprise the active compounds in an amount of from 1 to 80% by weight, may be used directly or after 100 to 10,000-fold dilution, or in the form of a chemical bath.

Furthermore, it has been found that the compounds of the formula (I) according to the invention show a potent insecticidal activity against insects which destroy industrial materials.

The following insects may be mentioned by way of example and as being preferred, but without posing any limitation:

beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec. Tryptodendron spec. *Apate monachus, Bostrychus capucins, Heterobostrychus brunneus,* Sinoxylon spec. *Dinoderus minutus* dermapterans, such as

*Sirex juvencus, Urocerus gigas, Urocerus gigas taignus, Urocerus augur* termites, such as

Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.

thrips, such as *Lepisma saccarina.*

Industrial materials are to be understood as meaning, in the present context, non-live materials such as, preferably, polymers, glues, sizes, papers and boards, leather, wood and derived timber products, and paints.

The material to be protected against attack by insects is very particularly preferably wood and derived timber products.

Wood and derived timber products which can be protected by the agent according to the invention, or by mixtures comprising it, are to be understood as meaning, for example, construction timber, wooden beams, railway sleepers, bridge components, jetties, wooden vehicles, boxes, pallets, containers, telegraph poles, wood laggings, windows and doors made of wood, plywood, particle boards, joiner's work, or timber products which, quite generally, are used in house building or in joinery.

The active compounds can be used as such, in the form of concentrates or generally customary formulations, such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellent, if appropriate dessicants and UV stabilizers and, if appropriate, colourants and pigments, and other processing auxiliaries.

The insecticides or concentrates used for the protection of wood and timber materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum amount used can be determined upon use in every single case by means of test series. However, in general it suffices to employ 0.0001 to 20% by weight, preferably 0.001 to 10% by weight, of the active compound based on the material to be protected.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

The organochemical solvents employed are preferably oily or oil-like solvents with an evaporation number of above 35 and a flash point of above 30° C., preferably above 45° C. Substances which are used as such oily and oil-like solvents of low volatility which are insoluble in water are suitable mineral oils or their aromatic fractions or mineral-oil-comprising solvent mixtures, preferably white spirit, petroleum and/or alkylbenzene.

It is advantageous to use mineral oils with a boiling range of from 170 to 220° C., white spirit with a boiling range of 170 to 220° C., spindle oil with a boiling range of from 250 to 350° C., petroleum or aromatics with a boiling range of from 160 to 280° C., spirit of turpentine, and the like.

In a preferred embodiment, the substances used are liquid aliphatic hydrocarbons with a boiling range of from 180 to 210° C. or high-boiling mixtures of aromatic and aliphatic hydrocarbons with a boiling range of from 180 to 220° C. and/or spindle oil and/or monochloronaphthalene, preferably α-monochloronaphthalene.

The organic oily or oil-like solvents of low volatility with an evaporation number of above 35 and a flash point of above 30° C., preferably above 45° C., can be replaced in part with organochemical solvents of medium or high volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents containing hydroxyl and/or ester and/or ether groups, such as, for example, glycol ethers, esters or the like.

Organochemical binders which are used within the scope of the present invention are the binding drying oils and/or synthetic resins which are known per se, can be diluted with water and/or are soluble, dispersible or emulsifiable in the organo-chemical solvents employed, in particular binders composed of or comprising an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene-cumarone resin, silicone resin, drying vegetable and/or drying oils and/or physically drying binders based on a natural and/or synthetic resin.

The synthetic resin used as binder can be employed in the form of an emulsion, dispersion or solution. Substances which can also be used as binders are bitumen or bituminous substances in amounts of up to 10% by weight. In addition, colourants, pigments, water repellents, odour-corrective agents and inhibitors or anticorrosives which are known per se can be employed, inter alia.

The composition or concentrate preferably comprises, in accordance with the invention, at least one alkyd resin or modified alkyd resin and/or a drying vegetable oil as the organochemical binder. Substances which are preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds or crystallization or precipitation. They preferably replace 0.01 to 30% of the binder (based on 100% of binder employed).

The plasticizers are from the chemical classes of the phthalic esters such as dibutyl phthalate, dioctyl phthalate or benzylbutyl phthalate, phosphoric esters such as tributyl phosphate, adipic esters such as di-(2-ethylhexyl) adipate, stearates such as butyl stearate or amyl stearate, oleates such as butyl oleate, glycerol ethers or higher-molecular-weight glycol ethers, glycerol esters, and p-toluenesulphonic esters.

Fixatives are based chemically on polyvinyl alkyl ethers such as, for example, polyvinyl methyl ether, or ketones such as benzophenone and ethylene-benzophenone.

Another suitable solvent or diluent is, in particular, water, if appropriate in a mixture with one or more of the abovementioned organochemical solvents or diluents, emulsifiers and dispersants.

Particularly effective protection of wood is achieved by means of industrial-scale impregnating processes, for example vacuum, double-vacuum or pressure processes.

If appropriate, the ready-to-use compositions can comprise other insecticides and, if appropriate, also one or more fungicides.

Additional components which may be admixed are preferably the insecticides and fungicides mentioned in Wo 94/29 268. The compounds mentioned in the above document are expressly part of the present application.

Components which may very particularly preferably be admixed are insecticides such as chlorpyriphos, phoxim, silafluofin, alphamethrin, cyfluthrin, cypermethrin, deltamethrin, permethrim, imidacloprid, NI-25, flufenoxuron, hexaflumuron and triflumuron, and fungicides such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octyl-isothiazolin-3-one and 4,5-dichloro-N-octylisothiazolin-3-one.

The preparation and use of the active compounds according to the invention can be seen from the examples which follow.

PREPARATION EXAMPLES

Example 1

Process a)

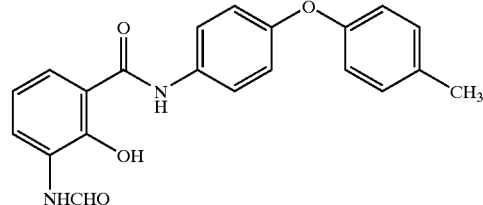

1.67 g (0.005 mol) of 3-(amino)-2-hydroxy-N-{4-[4-(methyl)-phenoxy]-phenyl}-benzamide are heated to boiling under reflux for 24 hours in 100 ml of formic acid. All of the solvent is distilled off under reduced pressure. This gives 0.72 g (40% of theory) of 3-(formylamino)-2-hydroxy-N-{4-[4-(-methyl)-phenoxy]-phenyl}-benzamide as an oil.

$^1$H-NMR: (CDCl$_3$/TMS): δ=6.80–7.85(m, 11H) ppm

PREPARATION OF THE STARTING COMPOUND

Example (II-1)

Process a-1a)

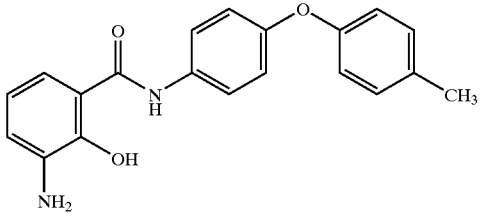

A solution of 1.3 g (0.0036 mol) of 3-nitro-2-hydroxy-N-[4-(4-methylphenoxy)-phenyl]-benzamide in 8 ml of methanol is treated with 0.1 g of Raney nickel and hydrogenated with hydrogen in an autoclave at 20° C. at a pressure of from 3 to 9 bar. Undissolved components of the mixture are filtered off, and the filtrate is evaporated to dryness under reduced pressure. This gives 0.67 g (56% of theory) of 3-amino-2-hydroxy-N-[4-(4-methylphenoxy)-phenyl]-benzamide.

$^1$H-NMR: (CDCl$_3$)/TMS): δ=6.73–7.99 (m, 11H) ppm

Example 2

Process b)

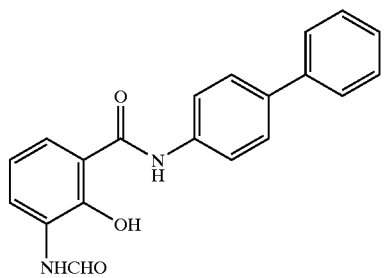

3 g (0.0099 mol) of 3-nitro-2-hydroxy-N-(4-phenylphenyl)-benzamide are treated with 0.4 g of 10% palladium-on-charcoal and 10 ml of water. 19 ml of formic acid are subsequently added dropwise and the mixture is heated for 2 hour at 110° C. After cooling, the catalyst is filtered off with suction and the residue washed with water. The filtrate is extracted using dichloromethane, the organic phase is separated off and dried over sodium sulphate, and the solvent is distilled off under reduced pressure. This gives 1.4 g (48% of theory) of 3-formamido-2-hydroxy-N-(4-phenylphenyl)-benzamide of melting point 190° C.

PREPARATION OF THE STARTING COMPOUND

Example IVa-1

Process b-1)

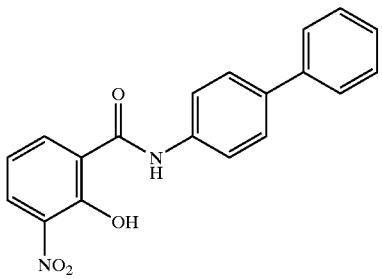

15 g (0.08 mol) of 3-nitrosalicylic acid, 13.8 g (0.08 mol) of 4-aminobiphenyl and 18.5 g (0.08 mol) of bicyclohexylcarbodiimide are introduced into 400 ml of pyridine, and the stirred mixture is heated for hours at 90° C. After the mixture has been cooled and filtered and the mixture concentrated, 200 ml of 10% strength hydrochloric acid are added, and the mixture is extracted using 200 ml of dichloromethane. The combined organic phases are dried over sodium sulphate and freed from solvent in vacuo. The residue is recrystallized from toluene.

This gives 16 g (60% of theory) of 3-nitro-2-hydroxy-N-(4-phenyl-phenyl)-benzamide as yellow crystals of melting point 152° C.

Example 3

Process c)

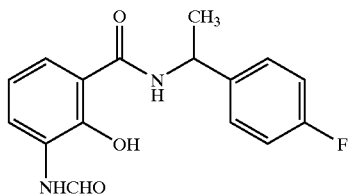

2.4 g (0.006 mol) of 3-nitro-2-benzyloxy-N-[-(4-fluorophenyl)-ethyl)-benzamide are treated with 0.6 g of 10% palladium-on-charcoal and 8 ml of water. 15 ml of formic acid and 0.9 g of tin powder are added in succession to this mixture, and the batch is subsequently refluxed for 5 hours. The solid components are then filtered off with suction and the filtrate is extracted using dichloromethane. The organic phase is dried over sodium sulphate and concentrated under reduced pressure. This gives 1.1 g (61% of theory) of 3-formamido-2-hydroxy-N-[1-(4-fluorphenyl)-ethyl]-benzamide as an oil.

$^1$H-NMR: (CDCl$_3$/TMS): δ=1.62 (d, 3H) ppm

PREPARATION OF THE STARTING COMPOUND

Example (V-1)

Process a-2)

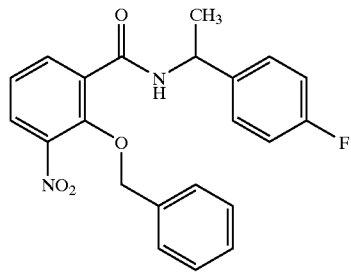

2.4 g (0.011 mol) of triethylamine are added at −10° C. to a solution of 3 g (0.011 mol) of 3-nitro-2-benzyloxybenzoic acid in 40 ml of dichloromethane. After the mixture has been stirred for 5 minutes, 2.8 g (0.011 mol) of isobutyl chloroformate are added dropwise at −10° C., and the mixture is stirred for a further 30 minutes. A solution of 1.53 g (0.011 mol) of 1-(4-fluorophenyl)-ethylamine in 10 ml of dichloromethane is added at −10° C., and stirring is continued for 12 hours without further cooling. The mixture is treated with sodium halogen carbonate solution, and the organic phase is separated off, washed with water and dried over sodium sulphate. After the solvent has been distilled off, 2.5 g (56% of theory) of 3-nitro-2-benzyloxy-N-[1-(4-fluorophenyl)-ethyl]-benzamide are obtained as an oil.

$^1$H NMR: (CDCl$_3$/TMS) δ=1.34 (d, 3H) ppm

Other compounds of the general formula (I) which are obtained analogously to Preparation Examples 1 to 3 and following the general description of the processes according to the invention are those listed in Table 1 below:

TABLE 1

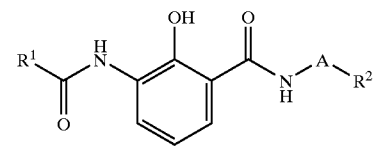

(I)

| Ex. No. | R$^1$ | A | R$^2$ | Physical data |
|---|---|---|---|---|
| 4 | H | — | ![2-chloro-4-methylphenyl 4-chlorophenyl ether] | NMR**: 6.90–8.54 (m, 12H) |
| 5 | H | — | ![4-methylphenyl 3-trifluoromethylphenyl ether] | m.p.: 100° C. |
| 6 | H | —CH$_2$— | ![4-methylphenyl] | MS*: m/e = 270(M$^+$) |
| 7 | H | CH(CH$_3$) | ![4-chloro-4-methylphenyl] | NMR**: 1.62 (d, 3H) |
| 8 | H | —CH$_2$—CH$_2$— | ![3,4-dimethoxy-4-methylphenyl] | NMR**: 3.85(s, 3H); 3.88(s, 3H) |
| 9 | H | CH(CH$_3$) | ![4-methylphenyl] | MS*: m/e = 284(M$^+$) |
| 10 | H | CH(CH$_3$) | ![3-methoxy-4-methylphenyl] | NMR**: 1.61(d, 3H) |

TABLE 1-continued (I)

| Ex. No. | R¹ | A | R² | Physical data |
|---|---|---|---|---|
| 11 | H | isobutyl (CH(CH₃)₂-CH₂-) | 4-OCH₃-phenyl | MS*: m/e = 314(M⁺) |
| 12 | H | sec-butyl-CH₂ (CH₃-CH₂-CH(CH₃)-CH₂-) | 4-OCH₃-phenyl | NMR**: 1.24(d, 3H) |
| 13 | H | —CH₂— | 3-Cl-phenyl | NMR**: 4.64(d, 2H) |
| 14 | H | —CH₂— | 4-OCH₃-phenyl | m.p.: 142° C. |
| 15 | H | isobutyl | 2,4-diCl-phenyl | m.p.: 74° C. |
| 16 | H | isobutyl | 4-C₂H₅-phenyl | NMR**: 1.62(d, 3H) |
| 17 | H | — | 4-Cl-phenyl | logp.: 2.53 |
| 18 | H | — | 3-CF₃-phenyl | MS*: m/e = 324(M⁺) |
| 19 | H | — | 3,5-bis(CF₃)-phenyl | MS*: m/e = 392(M⁺) |
| 20 | H | — | 3,5-diCl-phenyl | MS*: m/e = 324(M⁺ − 1) |

TABLE 1-continued (I)

$$R^1 \underset{O}{\overset{H}{\underset{\|}{N}}} \text{-}\underset{OH}{\underset{|}{\text{Ar}}}\text{-}\underset{O}{\overset{\|}{C}}\text{-}\underset{H}{\overset{}{N}}\text{-}A\text{-}R^2$$

| Ex. No. | R¹ | A | R² | Physical data |
|---|---|---|---|---|
| 21 | H | — | 3-Cl-5-CF₃-phenyl | MS*: m/e = 358(M⁺) |
| 22 | H | — | 5-Cl-2-methyl-3-NHCHO-phenyl | MS*: m/e = 333(M⁺) |
| 23 | H | — | 2-Cl-5-methyl-3-NHCHO-phenyl (isomer) | MS*: m/e = 333(M⁺) |
| 24 | H | — | Cyclododecyl | MS*: m/e = 346(M⁺) |
| 25 | H | — | Cyclohexyl | logp.: 2.36 |
| 26 | H | — | Cyclopentyl | logp.: 2.04 |
| 27 | H | — | Cyclopropyl | logp.: 1.36 |
| 28 | CH₃ | — | 4-Cl-phenyl | logp.: (not given) |
| 29 | CH₃ | — | 4-(4-methylphenoxy)-phenyl (bis-methyl diphenyl ether) | logp.: 3.49 |
| 30 | H | — | Cycloheptyl | logp.: 2.71 |
| 31 | H | —CH₂— | 2,4-dichlorophenyl | logp.: 2.86 |

TABLE 1-continued
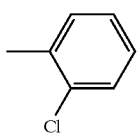
(I)
| Ex. No. | R¹ | A | R² | Physical data |
|---|---|---|---|---|
| 32 | H | —CH₂— |  | logp.: 2.44 |
| 33 | H | 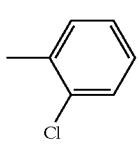 | 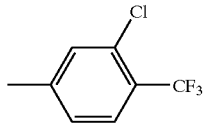 | ¹H-NMR**: 1.64(d, 3H) |
| 34 | H | —CH₂— |  | logp.: 2.94 |
| 35 | H | —CH₂— | 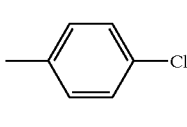 | m.p.: 103° C. |
| 36 | H | —CH₂— | 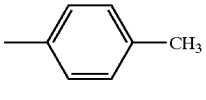 | logp.: 2.46 |
| 37 | H | —CH₂— | 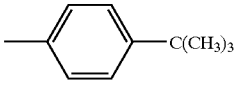 | logp.: 2.36 |
| 38 | H | —CH₂— | 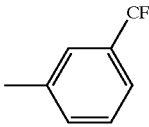 | logp.: 3.22 |
| 39 | H | —CH₂— | 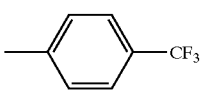 | m.p.: 110° C. |
| 40 | H | —CH₂— |  | logp.: 2.65 |
| 41 | H | —CH₂—CH₂— | 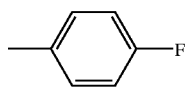 | m.p.: 140° C. |
| 42 | H | —CH₂—CH₂— |  | logp.: 2.32 |

TABLE 1-continued (I)

| Ex. No. | R¹ | A | R² | Physical data |
|---|---|---|---|---|
| 43 | H | —CH₂—CH₂— | 4-CH₃-phenyl | logp.: 2.59 |
| 44 | H | —CH₂—CH₂— | 3,4-diCl-phenyl | MS*: m/e = 352(M⁺) |
| 45 | H | —CH₂—CH₂— | 2-Cl-phenyl | logp: 2.57 |
| 46 | H | —CH₂—CH₂— | 3-phenoxyphenyl | |
| 47 | H | —CH₂—CH₂— | 4'-ethyl-biphenyl-4-yl | logp.: 5.26 |
| 48 | H | —CH₂—CH₂— | 4-C(CH₃)₃-phenyl | logp.: 3.50 |
| 49 | H | —CH₂—CH₂— | 3-(4-chlorophenoxy)phenyl | logp.: 3.55 |
| 50 | H | —CH₂—CH₂— | 4-(4-chlorophenoxy)phenyl | MS*: m/e = 410(M⁺) |
| 51 | H | iBu (CH(CH₃)₂ branch) | 2-Cl-phenyl | logp.: 2.62 |
| 52 | H | iBu | 3,4-diCl-phenyl | logp.: 3.03 |
| 53 | H | iBu | 4-CH₃-phenyl | logp.: 2.62 |

TABLE 1-continued (I)

| Ex. No. | R¹ | A | R² | Physical data |
|---|---|---|---|---|
| 54 | H | -CH(CH₃)-CH(CH₃)₂ (isobutyl) | 3-methylphenyl | logp.: 2.59 |
| 55 | H | isobutyl | 3-chlorophenyl | |
| 56 | H | isobutyl | 3-CF₃-phenyl | logp.: 2.85 |
| 57 | H | isobutyl | 2-OCH₃-phenyl | logp.: 2.02 |
| 58 | H | isobutyl | 2,3,5-trimethylphenyl | logp.: 3.09 |
| 59 | H | isobutyl | 3,4-dimethoxyphenyl | |
| 60 | H | isobutyl | 4-SO₂CH₃-phenyl | NMR**: 3.05(s, 3H) |
| 61 | H | isobutyl | 4-OC₂H₅-phenyl | |
| 62 | H | isobutyl | 4-phenoxyphenyl | logp.: 3.27 |
| 63 | H | isobutyl | 4-C(CH₃)₃-phenyl | logp.: 3.51 |

TABLE 1-continued (I)

R¹―C(O)―NH―[2-OH-benzene-1,3-diyl]―C(O)―NH―A―R²

| Ex. No. | R¹ | A | R² | Physical data |
|---|---|---|---|---|
| 64 | H | —CH(CH₃)—CH(CH₃)₂ (isobutyl, CH₃) | 4-N(CH₃)₂-phenyl | |
| 65 | H | isobutyl (CH₃) | 4-NHC(O)CH₃-phenyl | |
| 66 | H | isobutyl (CH₃) | 2,4-dimethylphenyl | logp.: 2.92 |
| 67 | H | —CH(C₂H₅)— (with CH₃) | 4-CH₃-phenyl | logp.: 2.92 |
| 68 | H | —CH(C₂H₅)— (with CH₃) | 4-OCH₃-phenyl | |
| 69 | H | —CH(C₂H₅)—CH(CH₃)—CH₂—CH₃ | 4-OCH₃-phenyl | |
| 70 | H | isobutyl (CH₃) | norbornyl | logp.: 3.14 |
| 71 | H | isobutyl (CH₃) | cyclohex-3-enyl | logp.: 3.06 |
| 72 | H | isobutyl (CH₃) | 5-chlorobenzofuran-2-yl | |
| 73 | H | isobutyl (CH₃) | thiophen-2-yl | |
| 74 | H | —CH₂— | 3,5-dimethylphenyl | logp.: 2.38 |

TABLE 1-continued
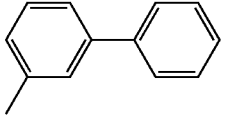
(I)
| Ex. No. | R¹ | A | R² | Physical data |
|---|---|---|---|---|
| 75 | H | — | 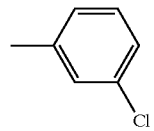 | |
| 76 | H | — | 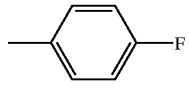 | logp.: 2.52 |
| 77 | H | — | 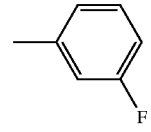 | logp.: 2.11 |
| 78 | H | — | 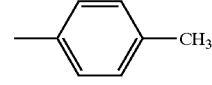 | logp.: 2.18 |
| 79 | H | — | 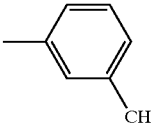 | logp.: 2.34 |
| 80 | H | — | 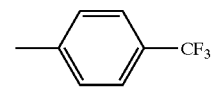 | logp.: 2.33 |
| 81 | H | — | 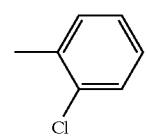 | logp.: 2.79 |
| 82 | H | — | 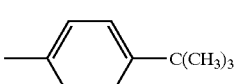 | logp.: 2.23 |
| 83 | H | — | 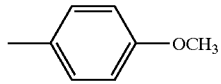 | logp.: 3.32 |
| 84 | H | — | 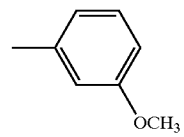 | |
| 85 | H | — |  | |

TABLE 1-continued (I)

| Ex. No. | R¹ | A | R² | Physical data |
|---|---|---|---|---|
| 86 | H | — | 4-methylphenyl-O-phenyl | logp.: 3.07 |
| 87 | H | — | 4-methylphenyl-O-(4-CF₃-phenyl) | logp.: 3.68 |
| 88 | H | — | 2-methylnaphthyl | logp.: 2.24 |
| 89 | H | — | 1-methylnaphthyl | logp.: 2.35 |
| 90 | H | — | 4-methylphenyl-O-CH₂-phenyl | MS*: m/e = 326(M⁺) |
| 91 | H | — | 4-methylbenzyl-O-phenyl | |
| 92 | H | — | 3-methylbenzyl-O-phenyl | logp.: 3.07 |
| 93 | H | — | 3-methylphenyl-O-CH₂-phenyl | NMR**: 5.30(s, 2H) |
| 94 | H | — | 3-methylphenyl-O-phenyl | logp.: 3.12 |

TABLE 1-continued
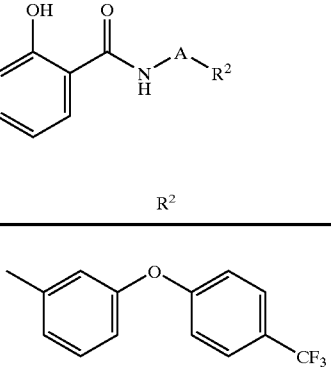
(I)
| Ex. No. | R¹ | A | R² | Physical data |
|---|---|---|---|---|
| 95 | H | — | 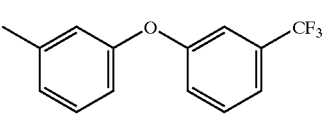 | logp.: 3.69 |
| 96 | H | — | 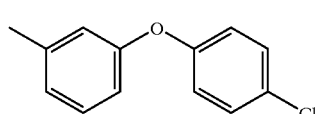 | |
| 97 | H | — | 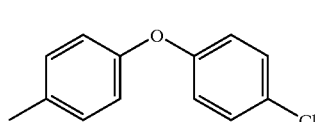 | logp.: 3.60 |
| 98 | H | — | 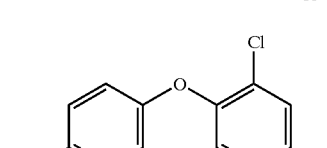 | logp.: 3.56 |
| 99 | H | — | 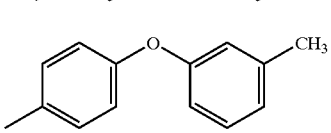 | logp.: 3.28 |
| 100 | H | — | 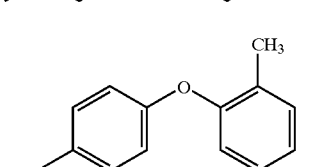 | logp.: 3.41 |
| 101 | H | — | 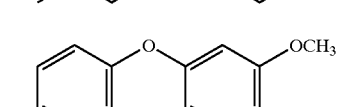 | logp.: 3.39 |
| 102 | H | — | 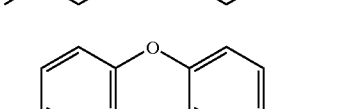 | |
| 103 | H | — | 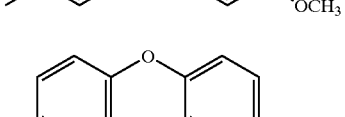 | |
| 104 | H | — | | |

TABLE 1-continued
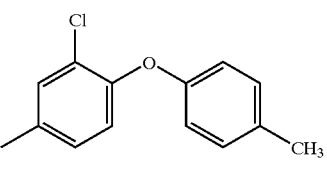
(I)
| Ex. No. | R¹ | A | R² | Physical data |
|---|---|---|---|---|
| 105 | H | — | 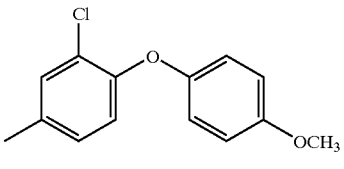 | |
| 106 | H | — | 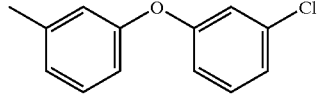 | |
| 107 | H | — | 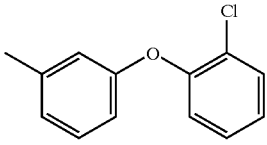 | logp.: 3.60 |
| 108 | H | — | 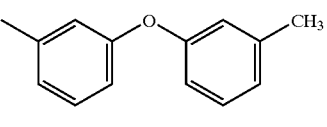 | |
| 109 | H | — | 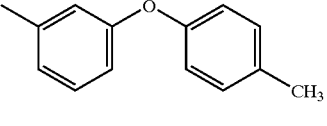 | logp.: 3.46 |
| 110 | H | — | 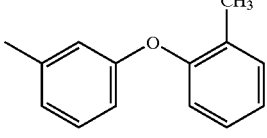 | logp.: 3.47 |
| 111 | H | — | 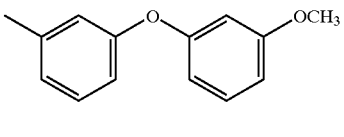 | |
| 112 | H | — | 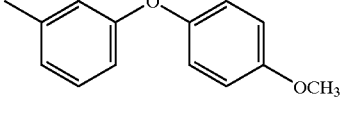 | |
| 113 | H | — | | |

TABLE 1-continued
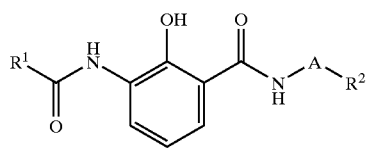
(I)
| Ex. No. | R¹ | A | R² | Physical data |
|---|---|---|---|---|
| 114 | H | — | 3-(4-OCHF₂-phenoxy)phenyl | |
| 115 | H | — | 3,5-dichloro-phenyl 4-chlorophenoxy | |
| 116 | H | — | 3,5-dichloro-phenyl 3-chlorophenoxy | |
| 117 | H | — | 3,5-dichloro-phenyl 2-chlorophenoxy | |
| 118 | H | — | 3,5-dichloro-phenyl 4-methylphenoxy | |
| 119 | H | — | 3,5-dichloro-phenyl 4-methoxyphenoxy | |
| 120 | H | — | 3,5-dimethyl-phenyl 4-chlorophenoxy | |
| 121 | H | — | 3,5-dimethyl-phenyl 4-methylphenoxy | |

TABLE 1-continued (I)

| Ex. No. | R¹ | A | R² | Physical data |
|---|---|---|---|---|
| 122 | H | — | 2-methyl-4-methylphenyl-O-(4-chlorophenyl) | logp.: 3.87 |
| 123 | H | — | 2-methyl-4-methylphenyl-O-(3-chlorophenyl) | NMR**: 2.23(s, 3H) |
| 124 | H | — | 2-methyl-4-methylphenyl-O-(4-methylphenyl) | logp.: 3.74 |
| 125 | H | — | 2-methyl-4-methylphenyl-O-(4-methoxyphenyl) | |
| 126 | H | — | 2-methyl-4-methylphenyl-O-(4-trifluoromethylphenyl) | |
| 127 | H | — | 2-methyl-4-methylphenyl-O-(3-trifluoromethylphenyl) | |
| 128 | H | — | 2-chloro-4-methylphenyl-O-(3-trifluoromethylphenyl) | |
| 129 | H | — | 2-fluoro-4-methylphenyl-O-(3-trifluoromethylphenyl) | |

TABLE 1-continued
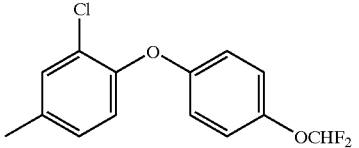
(I)
| Ex. No. | R¹ | A | R² | Physical data |
|---|---|---|---|---|
| 130 | H | — | 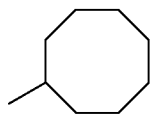 | |
| 131 | H | — | 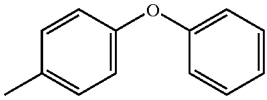 | logp.: 3.05 |
| 132 | H | —CH₂—CH₂— | 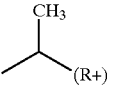 | logp.: 3.20 |
| 133 | H | 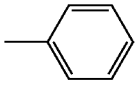 | 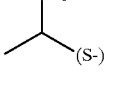 | logp.: 2.26 |
| 134 | H | 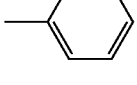 | 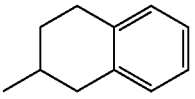 | logp.: 2.26 |
| 135 | H | — | 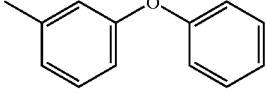 | logp.: 2.73 |
| 136 | H | —CH₂— | 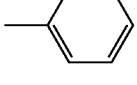 | logp.: 3.20 |
| 137 | H | —CH₂—CH₂— | 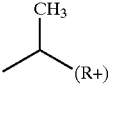 | logp.: 2.45 |
| 138 | H | 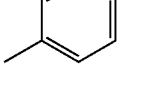 | 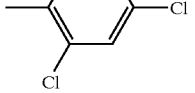 | logp.: 2.70 |
| 139 | H | H | 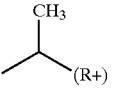 | logp.: 2.82 |
| 140 | H | 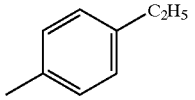 |  | logp.: 2.96 |

TABLE 1-continued (I)

| Ex. No. | R¹ | A | R² | Physical data |
|---|---|---|---|---|
| 141 | H | — | 2-benzylphenyl | logp.: 2.88 |
| 142 | H | — | 2-(trifluoromethyl)phenyl | logp.: 2.74 |
| 143 | H | — | 3,4-dichlorophenyl | logp.: 2.98 |
| 144 | H | — | 2-phenoxyphenyl | logp.: 3.00 |
| 145 | H | — | 2-methylphenyl | logp.: 2.66 |
| 146 | H | — | 4-bromo-2-fluorophenyl | logp.: 2.59 |
| 147 | H | —CH₂—CH₂— | 2,4-dichlorophenyl | logp.: 3.06 |
| 148 | H | — | 4-hydroxyphenyl | logp.: 1.30 |
| 149 | H | — | 2-fluorophenyl | logp.: 1.96 |

TABLE 1-continued

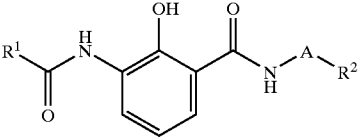

(I)

| Ex. No. | R¹ | A | R² | Physical data |
|---|---|---|---|---|
| 150 | H | — | 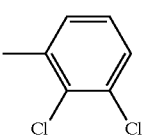 | NMR**: 12.43(s, 1H) |
| 151 | H | — | 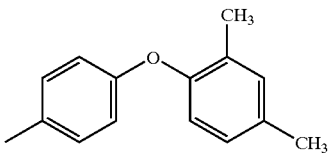 | logp.: 2.68 |
| 152 | H | — | 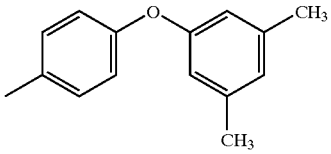 | logp.: 3.76 m.p.: 155° C. |
| 153 | H | — | 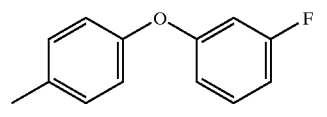 | logp.: 3.76 m.p.: 153° C. |
| 154 | H | — | 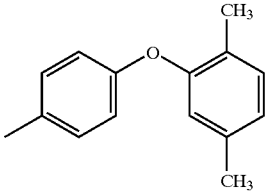 | logp.: 3.18 |
| 155 | H | — | 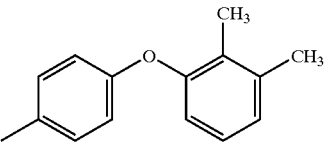 | logp.: 3.73 |
| 156 | H | — | | logp.: 3.66 |

*Mass spectrum
**The ¹H-NMR spectra were recorded in deuterochloroform ($CDCl_3$) or hexadeuterodimethyl sulphoxide (DMSO-$D_6$) with tetramethylsilane (TMS) as the internal standard. The data given are the chemical shift as δ-value in ppm.

Compounds of the general formula (II) which can be obtained analogously to Preparation Example (II-1) and following the general description of processes a-1a) and a-1b) according to the invention are those listed in Table 2 below:

TABLE 2

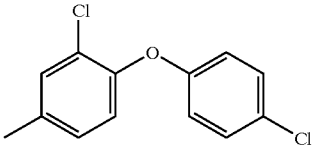

(II)

| Ex. No. | A | R² | Physical data |
|---|---|---|---|
| (II-2) | — | 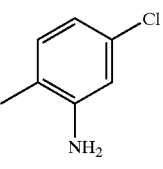 | NMR**: 6.73–7.99 (m, 10H) ppm |
| (II-3) | — | 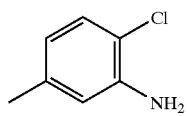 | MS*: m/e = 277 (M⁺) |
| (II-4) | — | 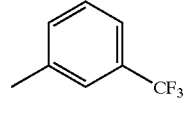 | MS*: m/e = 277 (M⁺) |
| (II-5) | — | 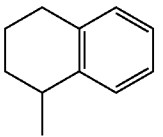 | MS*: m/e = 296 (M⁺) |
| (II-6) | — | 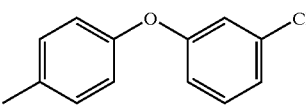 | HPLC***: Rf = 721 |
| (II-7) | — | 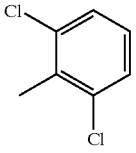 | HPLC***: Rf = 908 |
| (II-8) | — | 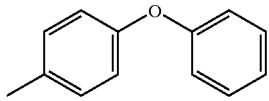 | NMR**: 7.71(s, 1H) |
| (II-9) | — | 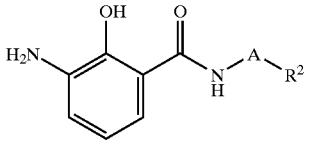 | logp.: 2.70 |

TABLE 2-continued

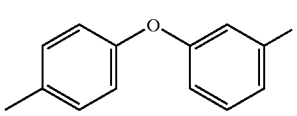

(II)

| Ex. No. | A | R² | Physical data |
|---|---|---|---|
| (II-10) | — | 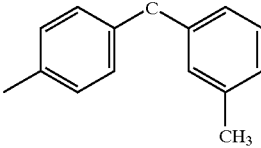 | logp.: 2.91 |
| (II-11) | — | 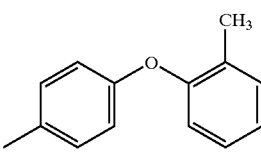 | logp.: 3.55 |
| (II-12) | — | 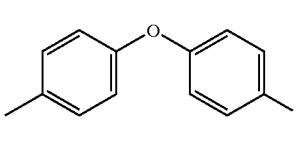 | logp.: 3.54 |
| (II-13) | — | 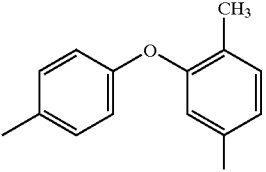 | ¹H-NMR**: 6.65–9.05 (m, 12H) |
| (II-14) | — |  | logp.: 3.49 |

*Mass spectrum
**The ¹H-NMR spectra were recorded in deuterochloroform (CDCl₃) or hexadeuterodimethyl sulphoxide (DMSO-D₆) with tetramethylsilane (TMS) as the internal standard. The data given are the chemical shift as δ-value in ppm.
***In the HPLC analysis, the retention index (Rf) is determined in a C₁₈ reversed-phase HPLC using the gradient system phosphoric acid (0.1% strength)/acetonitrile on the basis of 2-alkanones (C-3–C-16).

Compounds of the general formula (V) which can be obtained analogously to Preparation Example (V-1) and following the general description of process a-2) according to the invention are those listed in Table 3 below:

TABLE 3
(V)
| Ex. No. | A | R² | Physical data |
|---|---|---|---|
| (V-2) | CH(CH₃)₂-CH₂- | 4-Cl-C₆H₄- | m.p.: 128° C. |
| (V-3) | CH(CH₃)₂-CH₂- | 3-OCH₃-C₆H₄- | m.p.: 96° C. |
| (V-4) | CH(CH₃)₂-CH₂- | 4-OCH₃-C₆H₄- | m.p.: 118° C. |
| (V-5) | CH(CH₃)₂-CH₂- | 4-C₂H₅-C₆H₄- | m.p.: 100° C. |
| (V-6) | —CH₂—CH₂— | 3,4-(OCH₃)₂-C₆H₃- | m.p.: 100° C. |
| (V-7) | CH₃CH₂CH(CH₃)- | 4-OCH₃-C₆H₄- | m.p.: 84° C. |
| (V-8) | —CH₂— | 3-Cl-C₆H₄- | m.p.: 95° C. |
| (V-9) | CH(CH₃)₂-CH₂- | 2,4-Cl₂-C₆H₃- | m.p.: 128° C. |
| (V-10) | — | 4-Cl-C₆H₄- | m.p.: 138° C. |
| (V-11) | —CH₂— | 4-OCH₃-C₆H₄- | m.p.: 114° C. |

TABLE 3-continued
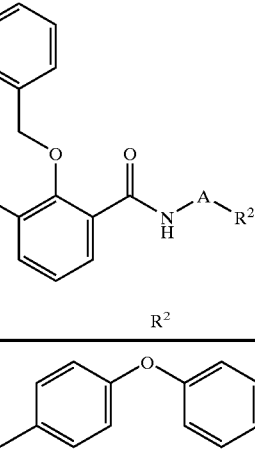
(V)
| Ex. No. | A | R² | Physical data |
|---|---|---|---|
| (V-12) | — | 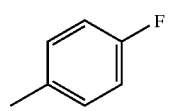 | logp.: 4.75 |
| (V-13) | —CH₂— | 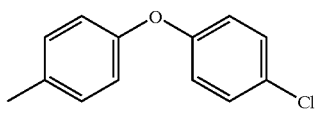 | m.p.: 138° C. |
| (V-14) | —CH₂—CH₂— | 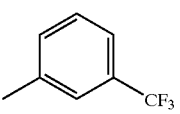 | m.p.: 119° C. |
| (V-15) | —CH₂— | 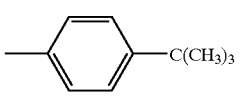 | m.p.: 92° C. |
| (V-16) | —CH₂—CH₂— | 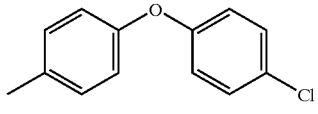 | logp.: 4.73 |
| (V-17) | —CH₂—CH₂— | 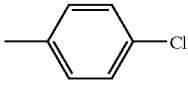 | m.p.: 84° C. |
| (V-18) | —CH₂—CH₂— | 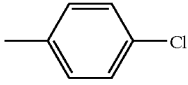 | m.p.: 125° C. |
| (V-19) | —CH₂— | 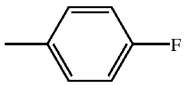 | m.p.: 146° C. |
| (V-20) | —CH₂—CH₂— | 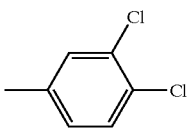 | m.p.: 98° C. |
| (V-21) | —CH₂—CH₂— | 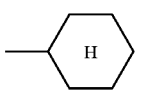 | m.p.: 108° C. |
| (V-22) | — |  | m.p.: 123° C. |

TABLE 3-continued
(V)
| Ex. No. | A | R² | Physical data |
|---|---|---|---|
| (V-23) | — | 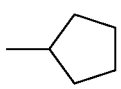 | m.p.: 146° C. |
| (V-24) | — | 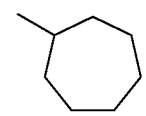 | m.p.: 108° C. |
| (V-25) | — | 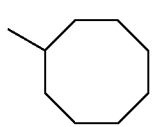 | m.p.: 111° C. |
| (V-26) | — | 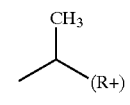 | m.p.: 78° C. |
| (V-27) | — | cyclodedecyl | m.p.: 130° C. |
| (V-28) | 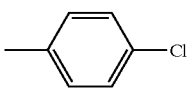 | 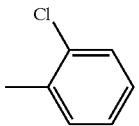 | logp.: 3.94 |
| (V-29) | —CH₂—CH₂— | 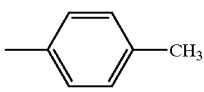 | logp.: 3.85 |
| (V-30) | —CH₂—CH₂— | 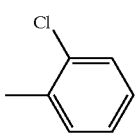 | logp.: 3.84 |
| (V-31) | —CH₂— | 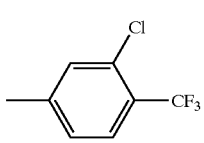 | logp.: 3.68 |
| (V-32) | —CH₂— | 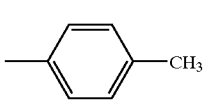 | logp.: 4.16 |
| (V-33) | —CH₂— |  | logp.: 3.64 |

TABLE 3-continued (V)

| Ex. No. | A | R² | Physical data |
|---|---|---|---|
| (V-34) | CH(CH₃)₂-CH₂- | 3-CF₃-C₆H₄- | logp.: 4.04 |
| (V-35) | CH(CH₃)₂-CH₂- | 4-C(CH₃)₃-C₆H₄- | logp.: 4.73 |
| (V-36) | CH(CH₃)₂-CH₂- | 2,4-(CH₃)₂-C₆H₃- | logp.: 4.19 |
| (V-37) | CH(CH₃)₂-CH₂- | 3,4-Cl₂-C₆H₃- | logp.: 4.29 |
| (V-38) | CH(CH₃)₂-CH₂- | cyclohex-3-enyl | logp.: 3.96 |
| (V-39) | —CH₂— | 4-C(CH₃)₃-C₆H₄- | logp.: 4.53 |
| (V-40) | CH(CH₃)₂-CH₂- | 4-CH₃-C₆H₄- | m.p.: 111° C. |
| (V-41) | CH(CH₃)₂-CH₂- | 3,5-(CH₃)₂-C₆H₃- | logp.: 3.87 |
| (V-42) | —CH₂— | 3-phenoxyphenyl | logp.: 4.21 |
| (V-43) | —CH₂—CH₂— | 4'-ethyl-biphenyl-4-yl | logp.: 6.30 |

TABLE 3-continued
(V)
| Ex. No. | A | R² | Physical data |
|---|---|---|---|
| (V-44) | 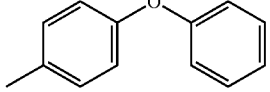 |  | m.p.: 92° C. |
| (V-45) | 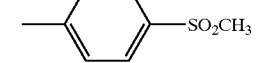 |  | m.p.: 45° C. |
| (V-46) | 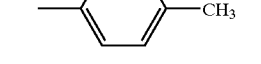 |  | m.p.: 89° C. |
| (V-47) | 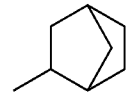 |  | m.p.: 120° C. |
| (V-48) | 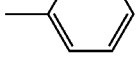 |  | m.p.: 113° C. |
| (V-49) | 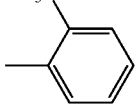 |  | m.p.: 121° C. |
| (V-50) | 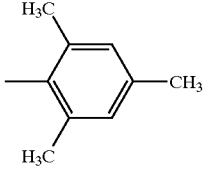 |  | m.p.: 104° C. |
| (V-51) | 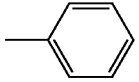 | 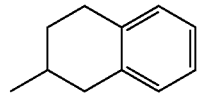 | m.p.: 118° C. |
| (V-52) | — |  | m.p.: 125° C. |
| (V-53) | 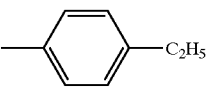 | | m.p.: 106° C. |

TABLE 3-continued
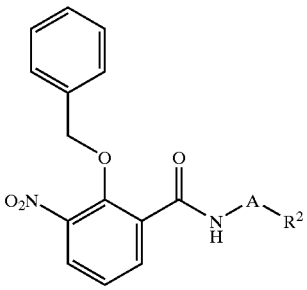
(V)
| Ex. No. | A | R² | Physical data |
|---|---|---|---|
| (V-54) | — | 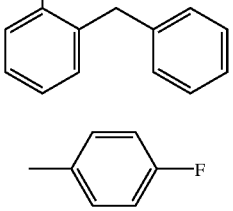 | logp.: 4.37 |
| (V-55) | — | 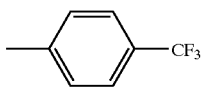 | logp.: 3.55 |
| (V-56) | — | 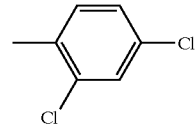 | logp.: 4.22 |
| (V-57) | —CH₂—CH₂— | 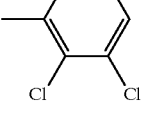 | logp.: 4.37 |
| (V-58) | — | 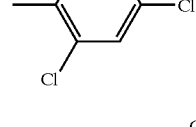 | logp.: 4.55 |
| (V-59) | —CH₂— | 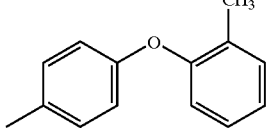 | logp.: 4.20 |
| (V-60) | — | 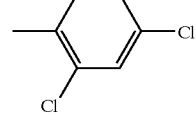 | logp.: 4.77 |
| (V-61) | — | 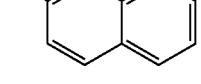 | logp.: 4.75 |
| (V-62) | — |  | logp.: 3.88 |

TABLE 3-continued (V)

2-benzyloxy-3-nitro-N-(A-R²)benzamide

| Ex. No. | A | R² | Physical data |
|---|---|---|---|
| (V-63) | — | 3-(benzyloxy)phenyl | logp.: 4.32 |
| (V-64) | — | 2-chlorophenyl | logp.: 4.06 |
| (V-65) | — | 3-chlorophenyl | logp.: 4.03 |
| (V-66) | — | 3-(trifluoromethyl)phenyl | logp.: 4.16 |
| (V-67) | — | 3,4-dichlorophenyl | logp.: 4.50 |
| (V-68) | — | 2-phenoxyphenyl | logp.: 4.60 |
| (V-69) | — | 3-phenoxyphenyl | logp.: 4.46 |
| (V-70) | — | 4-phenoxyphenyl | logp.: 4.42 |

TABLE 3-continued (V)

[Structure: 2-(benzyloxy)-3-nitro-N-(A-R²)benzamide]

| Ex. No. | A | R² | Physical data |
|---|---|---|---|
| (V-71) | — | 2-methylphenyl | logp.: 3.62 |
| (V-72) | — | 4-bromo-2-fluoro-phenyl (methyl substituted) | logp.: 4.33 |
| (V-73) | — | 4-(4-chlorophenoxy)phenyl | logp.: 5.76 |
| (V-74) | — | 3-fluorophenyl | logp.: 3.68 |
| (V-75) | — | 4-tert-butylphenyl | logp.: 4.74 |
| (V-76) | — | 4-(benzyloxy)phenyl | logp.: 4.32 |
| (V-77) | —CH₂— | 3-methylphenyl | logp.: 3.66 |
| (V-78) | —CH₂— | 4-(trifluoromethyl)phenyl | logp.: 3.95 |
| (V-79) | — | 4-methylphenyl | logp.: 3.82 |

TABLE 3-continued (V)

| Ex. No. | A | R² | Physical data |
|---|---|---|---|
| (V-80) | — | 3,5-dichlorophenyl | logp.: 4.76 |
| (V-81) | — | 3-(phenoxymethyl)phenyl | NMR**: 5.09(s, 2H) |
| (V-82) | — | 3-methylphenyl (with CH₃) | logp.: 4.41 |
| (V-83) | — | 3-(3-chlorophenoxy)phenyl | logp.: 4.97 |
| (V-84) | — | 3-(4-chlorophenoxy)phenyl | logp.: 4.93 |
| (V-85) | — | 1-methylnaphthyl | logp.: 3.88 |
| (V-86) | — | 3-(4-methylphenoxy)phenyl | logp.: 4.81 |
| (V-87) | — | 3-(3-methylphenoxy)phenyl | logp.: 4.80 |

TABLE 3-continued
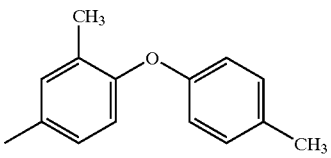
(V)
| Ex. No. | A | R² | Physical data |
|---|---|---|---|
| (V-88) | — | 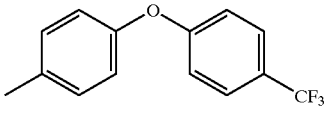 | logp.: 5.13 |
| (V-89) | — | 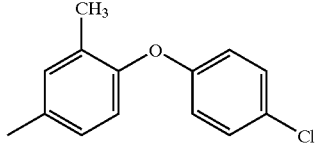 | logp.: 4.97 |
| (V-90) | — | 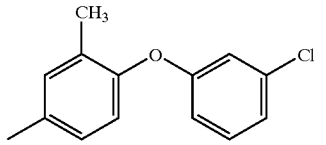 | logp.: 5.26 |
| (V-91) | — | 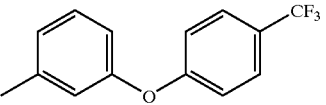 | logp.: 5.29 |
| (V-92) | — | 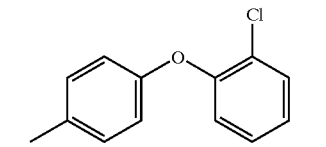 | logp.: 3.49 |
| (V-93) | — | 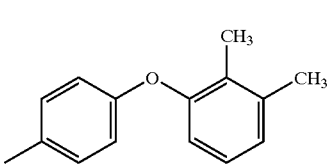 | logp.: 4.62 |
| (V-94) | — | 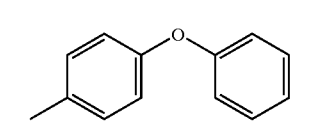 | logp.: 5.03 |
| (V-95) | — | | logp.: 4.41 |
The compounds of the general formula (IV-a) listed in Table 4 below are obtained analogously to Preparation Example (IV-a-1) and following the general description of process b-1) according to the invention:

TABLE 4

(IV-a)

3-nitro-2-hydroxy-N-(Z-R³)benzamide structure

| Ex. No. | Z | R³ | Physical data |
|---|---|---|---|
| IV-a-2 | — | cyclododecyl | MS*: m/e = 348 (M⁺) |
| IV-a-3 | — | 4-trifluoromethoxyphenyl | MS*: m/e = 342 (M⁺) |
| IV-a-4 | — | 3-trifluoromethylphenyl | MS*: m/e = 326 (M⁺) |
| IV-a-5 | — | 4-trifluoromethylphenyl | MS*: m/e = 326 (M⁺) |
| IV-a-6 | — | 2-trifluoromethylphenyl | MS*: m/e = 326 (M⁺) |
| IV-a-7 | — | 4-dodecylphenyl | IR: 1660 cm⁻¹ |
| IV-a-8 | — | 3-(difluorochloromethoxy)-phenyl | MS*: m/e = 358 (M⁺) |
| IV-a-9 | — | 3,4-(difluoromethoxy)-phenyl | MS*: m/e = 390 (M⁺) |
| IV-a-10 | —CH(CH₃)— | phenyl | MS*: m/e = 272 (M⁺ − 15) |
| IV-a-11 | —CH₂— | 2-chlorophenyl | MS*: m/e = 306.5 (M⁺) |
| IV-a-12 | —CH₂— | 2-fluorophenyl | MS*: m/e = 272 (M⁺ − 18) |
| IV-a-13 | —CH₂— | 4-methylphenyl | HPLC***: RF = 855 |
| IV-a-14 | —CH₂— | 2,6-dichlorophenyl | |
| IV-a-15 | —CH₂— | 4-methoxyphenyl | MS*: m/e = 302 (M⁺) |
| IV-a-16 | —CH₂— | 4-chlorophenyl | MS*: m/e = 306 (M⁺) |
| IV-a-17 | —CH₂— | 2,5-dimethylphenyl | MS*: m/e = 300 (M⁺) |
| IV-a-18 | —CH₂— | 4-tbutyl-phenyl | MS*: m/e = 328 (M⁺) |
| IV-a-19 | —CH(CH₃)— | 4-chlorophenyl | MS*: m/e = 321 (M⁺) |
| IV-a-20 | —CH₂— | 3-pyridyl | MS*: m/e = 273 (M⁺) |
| IV-a-21 | —CH₂— | 2-pyridyl | MS*: m/e = 273 (M⁺) |
| IV-a-22 | | 5-methyl-2,2-difluoro-benzo[1,3]dioxole | MS*: m/e = 338 (M⁺) |
| IV-a-23 | — | 1-methyl-1,2,3,4-tetrahydronaphthyl | MS*: m/e = 312 (M⁺) |
| IV-a-24 | — | 3,5-bistrifluoromethylphenyl | MS*: m/e = 394 (M⁺) |
| IV-a-25 | — | 4-methylphenyl-O-(3-trifluoromethylphenyl) | logP.: 4.23 |
| IV-a-26 | — | 4-phenylphenyl | logP: 3.80 |
| IV-a-27 | — | 4-methylphenyl-O-4-methylphenyl | logP: 4.06 |
| IV-a-28 | — | 4-methylphenyl-O-2-methylphenyl | logP: 4.04 |

TABLE 4-continued (IV-a)

Structure: 3-nitro-2-hydroxy-benzamide with N-H-Z-R³ substituent

| Ex. No. | Z | R³ | Physical data |
|---|---|---|---|
| IV-a-29 | — | 4-methyl-phenyl-O-(2-methoxyphenyl) | MS*: m/e = 380 (M⁺) |
| IV-a-30 | — | 2-naphthyl | logP: 3.33 |
| IV-a-31 | — | 2-benzylphenyl | logP: 3.61 |
| IV-a-32 | — | 3-benzyloxyphenyl | logP: 3.64 |
| IV-a-33 | — | 2-phenoxyphenyl | logP: 4.60 |
| IV-a-34 | — | 3-phenoxyphenyl | logP: 4.46 |
| IV-a-35 | — | 4-phenoxyphenyl | logP: 4.42 |
| IV-a-36 | — | 2,6-dichlorophenyl | logP: 3.74 |
| IV-a-37 | — | 4-bromo-2-fluorophenyl | logP: 4.33 |
| IV-a-38 | — | 4-methyl-phenyl-O-(4-chlorophenyl) | logP: 4.21 |
| IV-a-39 | — | 4-methyl-phenyl-O-(3-methylphenyl) | logP: 4.30 |
| IV-a-40 | — | 4-t-butylphenyl | logP: 4.74 |
| IV-a-41 | — | 4-benzyloxyphenyl | logP: 3.65 |
| IV-a-42 | —CH₂— | 3-methylphenyl | logP: 2.97 |
| IV-a-43 | —CH₂— | 4-trifluoromethylphenyl | logP: 3.23 |
| IV-a-44 | — | 4-trifluoromethylphenyl | logp: 3.39 |
| IV-a-45 | — | 3,5-dichlorophenyl | logP: 3.70 |
| IV-a-46 | — | 3-methyl-phenyl-CH₂-O-phenyl | ¹H-NMR**: δ = 12.5 ppm (s, 1H) |
| IV-a-47 | — | 3-methyl-phenyl-O-(3-chlorophenyl) | logP: 4.25 |
| IV-a-48 | — | 3-methyl-phenyl-O-(4-chlorophenyl) | logP: 4.22 |
| IV-a-49 | — | α-naphthyl | logP: 3.06 |
| IV-a-50 | — | 3-methyl-phenyl-O-(4-methylphenyl) | logP: 4.80 |

TABLE 4-continued (IV-a)

| Ex. No. | Z | R³ | Physical data |
|---|---|---|---|
| IV-a-51 | | 3-methylphenyl-O-3-methylphenyl | logP: 4.81 |
| IV-a-52 | | 2,4-dimethylphenyl-O-4-methylphenyl | logP: 5.13 |
| IV-a-53 | | 4-methylphenyl-O-4-trifluoromethylphenyl | logP: 4.97 |
| IV-a-54 | | 4-methylphenyl-O-2-chlorophenyl | logP: 4.62 |
| IV-a-55 | | 2,4-dimethylphenyl-O-4-chlorophenyl | logP: 4.51 |
| IV-a-56 | | 2,4-dimethylphenyl-O-3-chlorophenyl | logP: 4.53 |
| IV-a-57 | | 3-methylphenyl-O-4-trifluoromethylphenyl | 1H-NMR**: δ = 12.4 ppm (s, 1H) |
| IV-a-58 | | 4-methylphenyl-O-3,5-dimethylphenyl | logP: 4.39 |
| IV-a-59 | | 4-methylphenyl-O-2,4-dimethylphenyl | logP: 4.40 |

TABLE 4-continued (IV-a)

Structure: 2-hydroxy-3-nitro-benzamide with -NH-Z-R³ substituent

| Ex. No. | Z | R³ | Physical data |
|---|---|---|---|
| IV-a-60 | -CH₂- (p-tolyl) | -O-(3-F-phenyl) | logP: 3.80 |
| IV-a-61 | -CH₂- (p-tolyl) | -O-(4-F-phenyl) | logP: 3.72 |
| IV-a-62 | -CH₂- (p-tolyl) | -O-(2,5-diCH₃-phenyl) | logP: 4.39 |

*Mass spectrum
**The $^1$H-NMR spectra were recorded in deuterochloroform (CDCl$_3$) or hexadeuterodimethylsulphoxide (DMSO-D$_6$) using tetramethylsilane (TMS) as the internal standard. The data given are the chemical shift as δ value in ppm.
***In HPLC analysis, the retention index (Rf) is based on the 2-alkanones (C-3–C-16) using a C$_{18}$-reversed-phase HPLC and the gradient system phosphoric acid (0.1% strength)/acetonitrile.

USE EXAMPLES

Example: A

Sphaerotheca Test (Cucumber)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are dusted with conidia of the fungus *Sphaerotheca fuliginea*.

The plants are then placed in a greenhouse at 23 to 24° C. and at a relative atmospheric humidity of about 75%.

Evaluation is carried out 10 days after the inoculation.

In this test, an efficacy of over 80% is shown, for example, by the following compound (5) of the Preparation Examples at an active substance concentration of 100 ppm.

Example B

Venturia Test (Apple)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab pathogen *Venturia inaequalis* and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, an efficacy of over 80% is shown, for example, by the following compounds of the Preparation Examples (2), (4), (5), (12) and (15) at an active compound concentration of 100 ppm.

Example C

Pyricularia Test (Rice)/Protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. 4 days after the spray coating has dried on, the plants are inoculated with an aqueous spore suspension of *Pyricularia oryzae*. The plants are then placed in a greenhouse at 100% relative atmospheric humidity and 25° C.

Evaluation of the disease is carried out 4 days after the inoculation.

In this test, an efficacy of over 80% is shown, for example, by the following compound (5) of the Preparation Examples at an active compound concentration of 0.05%.

Example: D

*Pseudocercosporella herpotrichoides* Test (Wheat)/ Protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the rate of application shown. After the spray coating has dried on, the stem base of the plants is inoculated with spores of *Pseudocercosporella herpotrichoides.*

The plants are placed in a greenhouse at a temperature of approximately 10° C. and a relative atmospheric humidity of approximately 80%.

Evaluation is carried out 21 days after the inoculation.

In this test, an efficacy of over 80% is shown, for example, by the following compound (5) of the Preparation Examples at an active compound application rate of 250 g/ha.

Example E

Phytophthora Test (Tomato)/Protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous spore suspension of Phytophthora infestans.

The plants are placed in an incubation cabin at approximately 20° C. and 100% relative atmospheric humidity.

Evaluation is carried out 3 days after the inoculation.

In this test, an efficacy of over 80% is shown, for example, by the compounds 2, 4, 5, 10, 12 and 15 at an active compound concentration of 100 ppm.

Example F

Plasmopara Test (Grapevines)/Protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of *Plasmopara viticola* and then remain for 1 day in a humid chamber at 20 to 22° C. and 100% relative atmospheric humidity. The plants are then placed for 5 days in a greenhouse at 21° C. and an atmospheric humidity of approximately 90%. The plants are then moistened and placed in a humid chamber for 1 day.

Evaluation is carried out 6 days after the inoculation.

In this test, an efficacy of over 90% is shown, for example, by the compounds 5, 15 and 16 at an active compound concentration of 100 ppm.

Example G

Botrytis Test (Beans)/Protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, 2 small pieces of agar covered with *Botrytis cinerea* are placed on each leaf. The inoculated plants are then placed in a darkened humid chamber at 20° C. 3 days after the inoculation, the size of the lesions on the leaves is evaluated.

In this test, an efficacy of 90% is shown, for example, by the compounds 2, 3, 4, 5, 10, 12 15 and 16 at an active compound concentration of 500 ppm.

Example: H

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are populated with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, a destruction of 100% was shown, after 7 days, for example by the compounds of Preparation Examples (V-34) and (47) at an exemplary active compound concentration of 0.01%, while the known compound (A) showed no destruction.

Example: I

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration. Cabbage leaves (*Brassica oleracea*) are treated by being dipped into the preparation of the active compound of the desired concentration and are populated with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a destruction of 80 to 100% was shown, after 7 days, for example by the compounds of Preparation Examples (41), (39), (V-34), (14), (V-40), (V-51), (47), (131) and (37) at an exemplary active compound concentration of 0.01%.

Example: J

Spodoptera Test

Solvent: 7 parts by weight
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are populated with caterpillars of the fall armyworm *Spodoptera frugiperda* while the leaves are still moist.

After the specified period of time, the activity in % is determined. 100% means that all the caterpillars have been killed; 0% means that none of the caterpillars have been killed.

In this test, a destruction rate of 85% is shown, for example, by the following compound (47) after 7 days at an exemplary concentration of 0.1%.

Example: K

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of the active compound of the desired concentration and populated with larvae of the green rice leafhopper (*Nephotettix cincticeps*) while the seedlings are still moist.

After the specified period of time, the destruction in % is determined. 100% means that all the leafhoppers have been killed; 0% means that none of the leafhoppers have been killed.

In this test, a destruction of 100% was caused, after 7 days, for example by the compounds of Preparation Examples (39), (35) and (71) at an exemplary active compound concentration of 0.001%.

What is claimed is:
1. A compound of the formula (IVa)

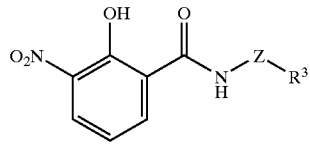

(IV-a)

in which
Z represents a single linkage or an alkylene chain and
R³ represents in each case optionally mono- to trisubstituted cycloalkyl, cycloalkenyl, aryl or heteroaryl having up to 3 hetero atoms, with the exception of the nitro group as substituent,
and excluding the compounds N-[3-chloro-4-(4-chlorophenoxy)phenyl]-2-hydroxy-3-nitro-benzamide,
N-(4-decylphenyl)-2-hydroxy-3-nitro-benzamide,
N-(3,4-dimethylphenyl)-2-hydroxy-3-nitro-benzamide,
3-nitro-N-phenethyl-salicylamide,
N-benzyl-3-nitro-salicylamide,
N-(4-aminophenyl)-2-hydroxy-3-nitro-benzamide,
N-(2-chloro-6-methylphenyl)-2-hydroxy-3-nitro-benzamide,
N-(3-chloro-2-methylphenyl)-2-hydroxy-3-nitro-benzamide,
2-hydroxy-3-nitro-N-(2,4,6-trichlorophenyl)-benzamide,
N-(2,3-dimethylphenyl)-2-hydroxy-3-nitro-benzamide,
N-(2-ethylphenyl)-2-hydroxy-3-nitro-benzamide,
2-hydroxy-3-nitro-N-phenyl-benzamide,
2-hydroxy-N-(4-methylphenyl)-3-nitro-benzamide,
2-hydroxy-N-(2-methylphenyl)-3-nitro-benzamide,
2-hydroxy-N-(4-methoxyphenyl)-3-nitro-benzamide,
2-hydroxy-N-(2-methoxyphenyl)-3-nitro-benzamide,
2-hydroxy-N-(2-hydroxyphenyl)-3-nitro-benzamide,
2-hydroxy-N-(2-hydroxyphenyl)-3-nitro-benzamide,
2-[(2-hydroxy-3-nitrobenzoyl)amino]-benzoic acid,
N-(2,6-dimethylphenyl)-2-hydroxy-3-nitro-benzamide,
N-(2,5-dimethylphenyl)-2-hydroxy-3-nitro-benzamide,
2-hydroxy-3-nitro-N-[2-phenoxy-5-(trifluoromethyl)phenyl]-benzamide,
N-[2-chloro-5-(trifluoromethyl)phenyl]-2-hydroxy-3-nitro-benzamide,
2-hydroxy-3-nitro-N-[4-(phenylazo)phenyl]-benzamide,
N-(2,4-dimethylphenyl)-2-hydroxy-3-nitro-benzamide,
N-(5-chloro-2-methoxyphenyl)-2-hydroxy-3-nitro-benzamide,
N-(4-chloro-2-methylphenyl)-2-hydroxy-3-nitro-benzamide,
N-(2-chloro-4-methylphenyl)-2-hydroxy-3-nitro-benzamide,
N-(4-bromo-2-methylphenyl)-2-hydroxy-3-nitro-benzamide,
N-(4-chloro-2,5-dimethoxyphenyl)-2-hydroxy-3-nitro-benzamide,
N-(2,5-dibromophenyl)-2-hydroxy-3-nitro-benzamide,
N-(2-fluorophenyl)-2-hydroxy-3-nitro-benzamide,
N-(3-fluorophenyl)-2-hydroxy-3-nitro-benzamide,
2-hydroxy-N-(2-iodophenyl)-3-nitro-benzamide,
2-hydroxy-N-(3-iodophenyl)-3-nitro-benzamide,
N-(2-bromophenyl)-2-hydroxy-3-nitro-benzamide,
N-(3-bromophenyl)-2-hydroxy-3-nitro-benzamide,
N-(2,5-dichlorophenyl)-2-hydroxy-3-nitro-benzamide, N-(3,4-dichlorophenyl)-2-hydroxy-3-nitro-benzamide,
2',3',5'-trichloro-6'-hydroxy-3-nitro-salicylanilide,
N-(p-hydroxy-a-methylphenethyl)-3-nitro-salicylamide,
3-nitro-3',5'-bis(trifluoromethoxy)-salicylanilide,
N-(2,4-dichlorophenyl)-2-hydroxy-3-nitro-benzamide,
2-hydroxy-N-(4-iodophenyl)-3-nitro-benzamide,
N-(4-bromophenyl)-2-hydroxy-3-nitro-benzamide,
N-(2-chlorophenyl)-2-hydroxy-3-nitro-benzamide,
N-(3-chlorophenyl)-2-hydroxy-3-nitro-benzamide,
N-(4-chlorophenyl)-2-hydroxy-3-nitro-benzamide and
N-(4-fluorophenyl)-2-hydroxy-3-nitro-benzamide.

2. A compound of the formula (IV-a) according to claim 1 in which

Z represents a single linkage, of methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), $R^3$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to trisubstituted by fluorine, chlorine, bromine, cyano, carboxyl, methyl, ethyl, methoxy, ethoxy, n- or i-propyl, methoxy-carbonyl or ethoxy-carbonyl, or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the enumeration which follows:

fluorine, chlorine, bromine, cyano, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethyl sulphonyloxy, hydroximinomethyl, hydroximinoethyl, methoximinomethyl, ethoximinomethyl, methoximinoethyl or ethoximinoethyl;

in each case divalent trimethylene(propane-1,3-diyl), tetramethylene(butane-1,4-diyl), methylenedioxy or ethylenedioxy, each of which is optionally monosubstituted to tetrasubstituted by identical or different substituents selected from the group consisting of fluorine, chlorine, methyl, trifluoromethyl, ethyl and n- or i-propyl, cyclopropyl, cyclobutyl, cyclopentyl or cyclohexyl, and/or phenyl, phenoxy, phenylalkyl, phenylthio, phenoxyalkyl, phenylthioalkyl, phenylallyloxy or phenylaik-yithio, each of which has 1 to 4 carbon atoms in the respective alkyl chains and each of which is optionally monosubstituted to tetrasubstituted by identical or different substituents selected from the group consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methyl sulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted or polysubstituted by identical or different substituents from the group consisting of fluorine, chlorine, methyl, trifluoromethyl, ethyl and n- or i-propyl, and cyclopropyl, cyclobutyl, cyclopentyl or cyclohexyl.

3. A compound of the formula (IV-a) according to claim 1 in which

Z represents a single linkage or methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), $R^3$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to trisubstituted by fluorine, chlorine, bromine, cyano, carboxyl, methyl, ethyl, methoxy, ethoxy, n- or i-propyl, methoxy-carbonyl or ethoxy-carbonyl;

or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the enumeration which follows:

fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylanmino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl,
in each case divalent trimethylene(propane-1,3-diyl), tetramethylene(butane-1,4-diyl), methylenedioxy or ethylenedioxy, each of which is optionally monosubstituted to tetrasubstituted by identical or different substituents selected from the group consisting of fluorine, chlorine, methyl, trifluoromethyl, ethyl and n- or i-propyl,
cyclopropyl, cyclobutyl, cyclopentyl or cyclohexyl, and/or phenyl, phenoxy, phenylthio, benzyl, phenylethyl, phenylpropyl, benzyloxy, benzylthio, phenoxymethyl, phenoxyethyl, phenylthiomethyl or phenylthioethyl, each of which is optionally monosubstituted to tetrasubstituted by identical or different substituents selected from the group consisting of
fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-Nmethylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl,
in each case divalent trimethylene(propane-1,3-diyl), tetramethylene(butane-1,4-diyl), methylenedioxy or ethylenedioxy, each of which is optionally monosubstituted or polysubstituted by identical or different substituents from the series consisting of fluorine, chlorine, methyl, trifluoromethyl, ethyl and n- or i-propyl, and cyclopropyl, cyclobutyl, cyclopentyl or cyclohexyl.

4. A compound of the formula (IV-a) according to claim 1 in which
Z represents a single linkage or methylene, 1,1-ethylene, 1,2-ethylene, 1-1-propylene, 1,2-propylene or 2,2-propylene,
$R^3$ represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted or disubstituted by methyl, ethyl, methoxy or ethoxy;
or represents in each case optionally monosubstituted to trisubstituted phenyl, naphthyl, furyl, benzofuranyl, pyrrolyl, indolyl, thienyl, benzothienyl, pyridyl, quinolyl, pyrimidyl, pyridazinyl or pyrazinyl, and the substituents being selected from the enumeration which follows:
fluorine, chlorine, bromine, cyano, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or ipropylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethyllsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethyl sulphonyloxy, methoximinomethyl, ethoximinomethyl, methoximinoethyl or ethoximinoethyl,
in each case divalent trimethylene(propane-1,3-diyl), tetramethylene(butane-1,4-diyl), methylenedioxy or ethylenedioxy, each of which is optionally monosubstituted to tetrasubstituted by identical or different substituents selected from the group consisting of fluorine, chlorine, methyl, trifluoromethyl, ethyl and n- or i-propyl,
and/or phenyl, phenoxy, phenylthio, benzyl, phenyl-1-ethyl, phenyl-2-ethyl, benzyloxy, benzylthio, phenoxymethyl or phenylthiomethyl, each of which is optionally monosubstituted to tetrasubstituted by identical or different substituents selected from the group consisting of
fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, and
in each case divalent trimethylene(propane-1,3-diyl), tetramethylene(butane-1,4-diyl), methylenedioxy or ethylenedioxy, each of which is optionally monosubstituted or polysubstituted by identical or different substituents selected from the group consisting of fluorine, chlorine, methyl, trifluoromethyl, ethyl and n- or i-propyl.

5. Compounds of the formula (V):

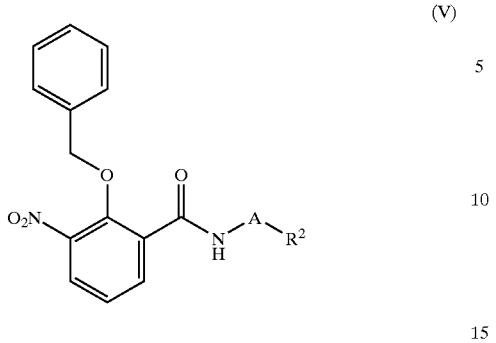

in which

A represents a single linkage or optionally substituted alkylene,

R² represents in each case optionally substituted cyloalkyl, cycloalkenyl, aryl or heterocyclyl, with the exception of the nitro group as substituent.

6. Process for the preparation of pesticides, comprising mixing compounds according to claim 1 with extenders and/or surface-active agents.

7. A pesticidal composition comprising a pesticidally effective amount of at least one compound according to claim 1 and an extender and/or surface-active agent.

8. A method of controlling a pest comprising applying to said pest or to a plant or industrial material from which it is desired to exclude such pests a pesticidally effective amount of at least one compound according to claim 1.

9. Compounds of the formula (II):

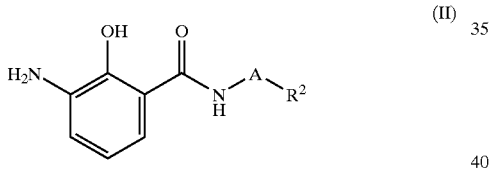

in which

A represents a single linkage or an alkylene chain having 1 to 6 carbon atoms,

R² represents cyclopropyl, cyclobutyl, cyclopentyl, cyclohexyl, cycloheptyl, cyclooctyl, cyclononyl, cyclodecyl, cycloundecyl, cyclododecyl, tetralinyl, decalinyl, cyclododecatrienyl, indanyl, norbornyl or adamantyl, each of which is optionally monosubstituted to hexasubstituted by fluorine, chlorine, bromine, cyano, carboxyl, methyl, ethyl, methoxy, ethoxy, n- or i-propyl, methoxy-carbonyl or ethoxy-carbonyl;

or represents in each case optionally monosubstituted to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents being selected from the enumeration which follows: fluorine, chlorine, bromine, cyano, formyl, carbamoyl, thiocarbamoyl, methyl ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimetylene(propane-1,3-diyl), tetramethylene(butane-1,4-diyl), methylenedioxy or ethylenedioxy, each of which is optionally monosubstituted to tetrasubstituled by identical or different substituents from the group consisting of fluorine, chlorine, methyl, trifluoromethyl, ethyl and n- or i-propyl, cyclopropyl, cyclobutyl cyclopentyl or cyclohexyl, and/or phenyl, phenoxy, phenylthio, benzyl, phenylethyl, phenylpropyl, benzyloxy, benzylthio, phenoxymethyl, phenoxyethyl, phenylthiomethyl or phenylthioethyl, each of which is optionally monosubstituted to tetrasubstituted by identical or different substituents from the group consisting of fluorine, chlorine, bromine, cyano, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluorometylthio, trifluoromethylsulphinyl or trifluoromethylsulphonyl, acetylamino, formylamino, N-formyl-N-methylamino, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, methoximinomethyl, ethoximinomethyl, methoximinoethyl or ethoximinoethyl, in each case divalent trimethylene(propane-1,3-diyl), tetramethylene(butane-1,4-diyl), methylenedioxy or ethylenedioxy, each of which is optionally monosubstituted or polysubstituted by identical or different substituents from the group consisting of fluorine, chlorine, methyl, trifluoromethyl, ethyl and n- or i-propyl, and cyclopropyl, cyclobutyl, cyclopentyl or cyclohexyl.

* * * * *